United States Patent
Mullick et al.

(10) Patent No.: US 9,157,082 B2
(45) Date of Patent: Oct. 13, 2015

(54) MODULATION OF APOLIPOPROTEIN CIII (APOCIII) EXPRESSION

(75) Inventors: Adam Mullick, Carlsbad, CA (US); Rosanne M. Crooke, Carlsbad, CA (US); Mark J. Graham, San Clemente, CA (US); Kenneth W. Dobie, Del Mar, CA (US); Richard Lee, Oceanside, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/114,187

(22) PCT Filed: Apr. 27, 2012

(86) PCT No.: PCT/US2012/035694
§ 371 (c)(1),
(2), (4) Date: Jan. 6, 2014

(87) PCT Pub. No.: WO2012/149495
PCT Pub. Date: Nov. 1, 2012

(65) Prior Publication Data
US 2014/0128453 A1    May 8, 2014

Related U.S. Application Data

(60) Provisional application No. 61/479,817, filed on Apr. 27, 2011, provisional application No. 61/595,009, filed on Feb. 3, 2012.

(51) Int. Cl.
| | | |
|---|---|---|
| *C12N 15/113* | (2010.01) | |
| *A61K 31/7088* | (2006.01) | |
| *A61K 45/06* | (2006.01) | |
| *A61K 31/713* | (2006.01) | |

(52) U.S. Cl.
CPC .......... *C12N 15/113* (2013.01); *A61K 31/7088* (2013.01); *A61K 31/713* (2013.01); *A61K 45/06* (2013.01)

(58) Field of Classification Search
USPC ........................................... 514/44; 536/24.5
See application file for complete search history.

(56) References Cited

U.S. PATENT DOCUMENTS

| | | | |
|---|---|---|---|
| 5,801,154 A | 9/1998 | Baracchini et al. | |
| 5,877,009 A | 3/1999 | Zannis et al. | |
| 5,998,148 A | 12/1999 | Bennett et al. | |
| 6,010,849 A | 1/2000 | Edwards et al. | |
| 6,184,212 B1 | 2/2001 | Miraglia et al. | |
| 6,300,132 B1 | 10/2001 | Monia et al. | |
| 6,500,672 B1 | 12/2002 | Sladek et al. | |
| 6,582,908 B2 | 6/2003 | Fodor et al. | |
| 6,852,536 B2 | 2/2005 | Dobie | |
| 7,227,014 B2 | 6/2007 | Crooke et al. | |
| 7,598,227 B2 | 10/2009 | Crooke et al. | |
| 7,750,141 B2 | 7/2010 | Crooke et al. | |
| 8,530,439 B2 | 9/2013 | Crooke et al. | |
| 2001/0053519 A1 | 12/2001 | Fodor et al. | |
| 2003/0228597 A1 | 12/2003 | Cowsert et al. | |
| 2004/0208856 A1 | 10/2004 | Crooke et al. | |
| 2004/0224304 A1 | 11/2004 | Berggren | |
| 2006/0264395 A1 | 11/2006 | Crooke et al. | |
| 2009/0081201 A1 | 3/2009 | Berggren | |

FOREIGN PATENT DOCUMENTS

| | | |
|---|---|---|
| WO | WO 92/10590 | 6/1992 |
| WO | WO 97/20924 | 6/1997 |
| WO | WO 03/011887 | 2/2003 |
| WO | WO 2004/093783 | 11/2004 |
| WO | WO 2010/083615 | 7/2010 |
| WO | WO 2010/107838 | 9/2010 |
| WO | WO 2012/149495 | 11/2012 |

OTHER PUBLICATIONS

Agrawal et al., "Antisense therapeutics: is it as simple as complementary base recognition?" Mol. Med. Today (2000) 6:72-81.

Alexander et al., "An Anisense Inhibitor of Apolipoprotein C-III Lowers Fasting Plasma Apolipoprotein C-III and Triglyceride Concentrations in Healthy Volunteers" Poster presented at American College of Cardiology meeting on Mar. 24-27, 2012.

Atzmon et al., "Lipoprotein Genotype and Conserved Pathway for Exceptional Longevity in Humans" PLOS Biology (2006) 4(4):562-569.

Bayarsaihan et al., "Single-strand-DNA-binding factors specifically recognize the pyrimidine element in the chick a2(I) collagen gene promoter" Biochem J. (1996) 314:293-296.

Bennett et al., "Inhibition of Endothelial Cell Adhesion Molecule Expression with Antisense Oligonucleotides" Journal of Immunology (1994) 152:3530-3540.

Braasch et al., "Novel Antisense and Peptide Nucleic Acid Strategies for Controlling Gene Expression" Biochem. (2002) 41(14):4503-4510.

Branch, "A good antisense molecule is hard to find" TIBS (1998) 23:45-50.

Brunzell, "The interaction of familial and secondary causes of hypertriglyceridemia: Role in pancreatitis" Journal of Clinical Lipidology (2012) 6:409-412.

Carpentier et al., "Effect of Alipogene Tiparvovec (AAV1-LPLS447X) on Postprandial Chylomicron Metabolism in Lipoprotein Lipase-Deficient Patients" J. Clin. Endocrin. Metab. (2012) 97(5):1635-1644.

(Continued)

*Primary Examiner* — Terra C Gibbs
(74) *Attorney, Agent, or Firm* — Isis Pharmaceuticals, Inc.

(57) ABSTRACT

Provided herein are methods, compounds, and compositions for reducing expression of ApoCIII mRNA and protein in an animal. Also provided herein are methods, compounds, and compositions for increasing HDL levels and/or improving the ratio of TG to HDL and reducing plasma lipids and plasma glucose in an animal. Such methods, compounds, and compositions are useful to treat, prevent, delay, or ameliorate any one or more of cardiovascular disease or metabolic disorder, or a symptom thereof.

45 Claims, No Drawings

(56) References Cited

OTHER PUBLICATIONS

Chan et al., "Apolipoprotein B-100 kinetics in visceral obesity: Associations with plasma apolipoprotein C-III concentration" Metabolism Clinical and Experimental (2002) 51(8):1041-1046.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chiuve et al., "Effect of the combination of methyltestosterone and esterified estrogens compared with esterified estrogens alone on apolipoprotein CIII and other apolipoproteins in very low density, low density, and high density lipoproteins in surgically postmenopausal women" J. Clin. Endocrinol. Metab. (2004) 89(5):2207-2213.

Crooke, "Progress in Antisense Technology" Ann. Rev. Med. (2004) 55:61-95.

Crooke, "Antisense oligonucleotides as therapeutics for hyperlipidaemias" Expert Opinion on Biological Therapy (2005) 5(7):907-917.

Crooke et al., "Basic Principles of Antisense Therapeutics" Antisense Research and Application (1998) Chapter 1:1-50.

Cuchel et al., "Inhibition of Microsomal Triglyceride Transfer Protein in Familial Hypercholesterolemia" New England Journal of Medicine (2007) 356:148-156.

Dammerman et al., "An apolipoprotein CIII haplotype protective against hypertriglyceridemia is specified by promoter and 3'untranslated region polymorphisms" Proc. Natl. Acad. Sci. U.S.A., (1993) 90:4562-4566.

De Grooth et al., "A review of CETP and its relation to atherosclerosis" J. Lipid. Res. (2004) 45(11):1967-1974.

De Silva et al., "Overexpression of human apolipoprotein C-III in transgenic mice results in an accumulation of apolipoprotein B48 remnants that is corrected by excess apolipoprotein E" J. Biol. Chem. (1994) 269:2324-2335.

Deere et al., "Antisense Phosphorodiamidate Morpholino Oligomer Length and Target Position Effects on Gene-Specific Inhibition in *Escherichia coli*" Antimicrobial Agents and Chemotherapy (2005) 49(1):249-255.

Duivenvoorden et al., "Apolipoprotein C3 Deficiency Results in Diet-Induced Obesity and Aggravated Insulin Resistance in Mice" Diabetes (2005) 54:664-671.

Funatsu et al., "Reduction in hepatic non-esterified fatty acid concentration after long-term treatment with atorvastatin lowers hepatic triglyceride synthesis and its secretion in sucrose-fed rats" Biochimica et Biophysica Acta (2002) 1580(2-3):161-170.

Gaudet et al., "Efficacy and long-term safety of alipogene tiparvovec (AAV1-LPLS447X) gene therapy for lipoprotein lipase deficiency: an open-label trial." Gene. Ther. (2013) 20(4):361-369.

GenBank Accession No. NT_035088.1, Aug. 1, 2002, from the NCBI website: http://www.ncbi.nlm.nih.gov/nuccore/NT_035088. 1?report=genbank, printout on Jan. 16, 2014.

Gewirtz et al., "Facilitating oligonucleotide delivery: Helping antisense deliver on its promise" PNAS USA (1996) 93:3161-3163.

Hernandez et al., "Regulation of hepatic ApoC3 expression by PGC-1beta mediates hypolipidemic effect of nicotinic acid" Cell. Metab. (2010) 12(4):411-419.

Hertz et al., "Mode of action of peroxisome proliferators as hypolipidemic drugs. Suppression of apolipoprotein C-III" J. Biol. Chem. (1995) 270:13470-13475.

Ito et al., "Hypertriglyceridemia as a result of human apo CIII gene expression in transgenic mice" Science (1990) 249:790-793.

Jen et al., "Suppression of Gene Expression by Targeted Disruption of Messenger RNA: Available Options and Current Strategies" Stem Cells (2000) 18:307-319.

Jensen et al., "Apolipoprotein C-III as a Potential Modulator of the Association Between HDL-Cholesterol and Incident Coronary Heart Disease" Journal of the American Heart Association (2012) 1:jah3-e000232.

Jong et al., "Role of ApoCs in Lipoprotein Metabolism—Functional Differences Between ApoC1, ApoC2, and ApoC3" Arterioscler. Thromb. Vasc. Biol. (1999) 19:472-484.

Jover et al., "Cytochrome P450 regulation by hepatocyte nuclear factor 4 in human hepatocytes: a study using adenovirus-mediated antisense targeting" Hepatology (2001) 33(3):668-675.

Karathanasis "Apolipoprotein multigene family: tandem organization of human apolipoprotein AI, CIII, and AIV genes" PNAS (1985) 82:6374-6378.

Kardassis et al., "Direct physical interactions between HNF-4 and Sp1 mediate synergistic transactivation of the apolipoprotein CIII promoter" Biochemistry (2002) 41:1217-1228.

Kardassis et al., "SMAD proteins transactivate the human ApoCIII promoter by interacting physically and functionally with hepatocyte nuclear factor 4" J. Biol. Chem. (2000) 275:41405-41414.

Klein et al., "P284: Apoprotein C-III (ApoCIII) Protein Concentrations and Gene Polymorphisms in Type 1 Diabetes" Aretioscler. Thromb. Vasc. Biol. (2002) 22(5):A-50.

Mayo Clinic Proceedings, Oct. 1, 1998, pp. 1-10. Hyperlipidemia and diabetes mellitus.

Levy-Wilson et al., "Isolation and DNA sequence of full-length cDNA for human preapolipoprotein CIII" DNA (1984) 3:359-364.

Li et al., "Common genetic variation in the promoter of the human apo CIII gene abolishes regulation by insulin and may contribute to hypertriglyceridemia" J. Clin. Invest. (1995) 96:2601-2605.

Maeda et al., "Molecular cloning of a human apoC-III variant: Thr 74—Ala 74 mutation prevents O-glycosylation" J. Lipid Res. (1987) 28:1405-1409.

Maeda et al., "Targeted disruption of the apolipoprotein C-III gene in mice results in hypotriglyceridemia and protection from postprandial hypertriglyceridemia" J. Biol. Chem. (1994) 269:23610-23616.

Lai et al., "Association Between Obesity and Hyperlipidemia Among Children" Yale Journal of Biology and Medicine (2001) 74:205-210.

New England Biolabs 1998/99 Catalog (cover page and pp. 121 and 284).

Nielsen, "Systemic Delivery: The Last Hurdle?" Gene Therapy (2005) 12:956-957.

Ogami et al., "Purification and characterization of a heat stable nuclear factor CIIIB1 involved in the regulation of the human ApoC-III gene" J. Biol. Chem. (1991) 266:9640-9646.

Olivieri et al., "ApoC-III gene polymorphisms and risk of coronary artery disease" J. Lipid. Res. (2002) 43:1450-1457.

Olivieri et al., "Apolipoprotein C-III, n-3 Polyunsaturated Fatty Acids, and "Insulin-Resistant" T-455C APOC3 Gene Polymorphism in Heart Disease Patients: Example of Gene-Diet Interaction" Clin. Chem. (2005) 51(2):360-367.

Opalinska et al., "Nucleic-Acid Therapeutics: Basic Principles and Recent Applications" Nature Rev. Drug Discov. (2002) 1:503-514.

Petersen et al., "Apolipoprotein C3 Gene Variants in Nonalcoholic Fatty Liver Disease" The New England Journal of Medicine (2010) 362(12):1082-1089.

Pollin et al., "A Null Mutation in Human APOC3 Confers a Favorable Plasma Lipid Profile and Apparent Cardioprotection" Science (2008) 322:1702-1705.

Protter et al., "Isolation and sequence analysis of the human apolipoprotein CIII gene and the intergenic region between the apo AI and apo CIII genes" DNA (1984) 3:449-456.

Raspe et al., "Identification of Rev-erb alpha as a physiological repressor of apoC-III gene transcription" J. Lipid. Res. (2002) 43:2172-2179.

Reynolds et al., "Rational siRNA design for RNA interference" Nature Biotechnology (2004) 22(3):326-330.

Roglans et al., "Atorvastatin Treatment Induced Peroxisome Proliferator-Activated Receptor Alpha Expression and Decreased Plasma Nonesterified Fatty Acids and Liver Triglyceride in Fructose-Fed Rats" Journal of Pharmacology and Experimental Therapeutics (2002) 302:232-239.

Sanghvi et al., "Heterocyclic Base Modifications in Nucleic Acids and Their Applications in Antisense Oligonucleotides" Antisense Research and Applications (1993) pp. 273-288.

(56) References Cited

OTHER PUBLICATIONS

Schoonjans et al., "3-Hydroxy-3-methylglutaryl CoA reductase inhibitors reduce serum triglyceride levels through modulation of apolipoprotein C-III and lipoprotein lipase" FEBS Lett. (1999) 452:160-164.

Senior, "Antisense inhibitor provides new treatment approach for hypercholesterolaemia" DDT (2002) 7(16):840-841.

Shachter "Apolipoproteins C-I and C-III as important modulators of lipoprotein metabolism" Curr. Opin. Lipidol. (2001) 12:297-304.

Sharpe et al., "Human apolipoproteins AI, AII, CII and CIII. cDNA sequences and mRNA abundance" Nucleic Acids Res. (1984) 12(9):3917-3932.

Tamm et al., "Antisense therapy in oncology: new hope for an old idea?" The Lancet (2001) 358:489-497.

Ugawa et al., "YM-53601, a novel squalene synthase inhibitor, suppresses lipgenic biosynthesis and lipid secretion in rodents" British Journal of Pharmacology (2003) 139:140-146.

Voight et al., "Plasma HDL choleserol and risk of myocardial infarction: a mendelian randomisaion study" The Lancet (2012) 380:572-580.

Vu-Dac et al., "Retinoids increase human apo C-III expression at the transcriptional level via the retinoid X receptor. Contribution to the hypertriglyceridemic action of retinoids." J. Clin. Invest. (1998) 102:625-632.

Webster's II New Riverside University Dictionary (1994) The Riverside Publishing Company, pp. 933 & 944.

Yuan et al., "Hypertriglyceridemia: its etiology, effects and treatment" CMAJ (2007) 176(8): 1113-1120.

Supplementary European Search Report for EP 04749914.0 dated Jan. 5, 2009.

International Search Report from application PCT/US04/10946 dated Feb. 22, 2006.

International Search Report from application PCT/US2012/035694 dated Jul. 19, 2012.

Subramaniam et al., "ApoC-III antisense oligonucleotides reduce liver mRNA and serum triglyceride levels in hypertriglyceridemic rats." Diabetes (2005) 54, Supplement 1, p. A233 (abstract).

Dias et al., "Antisense Oligonucleotides: Basic Concepts and Mechanisms" Molecular Cancer Therapeutics (2002) 1: 347-355.

Staels et al., "Fibrates Downregulate Apolipoprotein C-III Expression Independent of Induction of Peroxisomal Acyl Coenzyme A Oxidase" J. clin. Invest. (1995) 95: 705-712.

Graham et al., Antisense Inhibition of ApoC-III in Rhesus Monkeys Reduces Plasma Triglycerides and Raises HDL-C Without increasing Hepatic Fat: Circulation Research (2011) 109(12): p. E60.

Graham et al., "Antisense Oligonucleotide Inhibition of Apolipoprotein C-III Reduces Plasma Triglycerides in Rodents, Nonhuman Primates, and Humans" Circulation Research (2013) 112(11):1479-1490.

Mullick et al. "Antisense oligonucleotide reduction of apoB-ameliorated atherosclerosis in LDL receptor-deficient mice" J. of Lipid Research (2011) 52(5):885-896.

MODULATION OF APOLIPOPROTEIN CIII (APOCIII) EXPRESSION

CROSS REFERENCED TO RELATED APPLICATIONS

This application is a U.S. National Phase filing under 35 U.S.C. §371 claiming priority to international Serial No. PCT/US2013/035694 filed Apr. 27, 2012, which claims priority to U.S. Provisional Application 61/595,009, filed Feb. 3, 2012, and U.S. Provisional Application 61/479,817, filed Apr. 27, 2012, each of which is incorporated herein by reference in its entirety.

SEQUENCE LISTING

The present application is being filed along with a Sequence Listing in electronic format. The Sequence Listing is provided as a file entitled BIOL0130USASEQ.txt, created on Oct. 25, 2013 which is 8 Kb in size. The information in the electronic format of the sequence listing is incorporated herein by reference in its entirety.

FIELD OF THE INVENTION

Provided herein are methods, compounds, and compositions for reducing expression of Apolipoprotein CIII (ApoCIII) mRNA and protein, and increasing HDL or HDL activity in an animal. Also, provided herein are methods, compounds, and compositions for an ApoCIII inhibitor for reducing ApoCIII related diseases or conditions in an animal.

BACKGROUND

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

Apolipoprotein C-III (ApoCIII) is a constituent of HDL and of triglyceride (TG)-rich lipoproteins. Elevated ApoCIII is associated with hypertriglyceridemia. Accordingly, ApoCIII has a role in hypertriglyceridemia, a risk factor for coronary artery disease (Davidsson et al., J. Lipid Res. 2005. 46: 1999-2006). ApoCIII slows clearance of triglyceride-rich lipoproteins by inhibiting lipolysis, both through inhibition of lipoprotein lipase and by interfering with lipoprotein binding to cell-surface glycosaminoglycan matrix (Shachter, Curr. Opin. Lipidol., 2001, 12, 297-304).

The gene encoding human apolipoprotein C-III (also called APOC3, APOC-III, ApoCIII, and APO C-III) was cloned in 1984 by three research groups (Levy-Wilson et al., DNA, 1984, 3, 359-364; Protter et al., DNA, 1984, 3, 449-456; Sharpe et al., Nucleic Acids Res., 1984, 12, 3917-3932). The coding sequence is interrupted by three introns (Protter et al., DNA, 1984, 3, 449-456). The human ApoCIII gene is located approximately 2.6 kb to the 3' direction of the apolipoprotein A-1 gene and these two genes are convergently transcribed (Karathanasis, Proc. Natl. Acad. Sci. U.S.A., 1985, 82, 6374-6378). Also cloned was a variant of human apolipoprotein C-III with a Thr74 to Ala74 mutation from a patient with unusually high level of serum apolipoprotein C-III. As the Thr74 is O-glycosylated, the Ala74 mutant therefore resulted in increased levels of serum ApoCIII lacking the carbohydrate moiety (Maeda et al., J. Lipid Res., 1987, 28, 1405-1409). Other variants or polymorphisms that modulated Apo CIII expression were later identified. Some of the polymorphsims elevated ApoCIII. Elevated ApoCIII levels were associated with elevated triglyceride (TG) levels and diseases such as cardiovascular disease, metabolic syndrome, obesity and diabetes (Chan et al., Int J Clin Pract, 2008, 62:799-809; Onat et al., Atherosclerosis, 2003, 168:81-89; Mendivil et al., Circulation, 2011, 124:2065-2072).

Five polymorphisms have been identified in the promoter region of the gene: C (at position −641 of the gene) to A, G (at position −630 of the gene) to A, T (at position −625 of the gene) to deletion, C (at position −482 of the gene) to T and T (at position −455 of the gene) to C. All of these polymorphisms are in linkage disequilibrium with the SstI polymorphism in the 3' untranslated region. The SstI polymorphic site distinguishes the S1 and S2 alleles and the S2 allele has been associated with elevated plasma triglyceride levels (Dammerman et al., Proc. Natl. Acad. Sci. U.S.A., 1993, 90, 4562-4566). The ApoCIII promoter is downregulated by insulin and this polymorphic site abolishes the insulin regulation. Thus the potential overexpression of ApoCIII resulting from the loss of insulin regulation may be a contributing factor to the development of hypertriglyceridemia associated with the S2 allele (Li et al., J. Clin. Invest., 1995, 96, 2601-2605). The T (at position −455 of the gene) to C polymorphism has been associated with an increased risk of coronary artery disease (Olivieri et al., J. Lipid Res., 2002, 43, 1450-1457). Other polymorphisms in the human ApoCIII gene that have been associated with elevated ApoCIII and/or triglyceride expression include: C (at position 1100) to T, C (at position 3175) to G, T (at position 3206) to G, C (at positions 3238) to G, etc. (Tilly et al., J. Lipid Res., 2003, 44:430-436; Waterworth et al., Arterioscler Thromb Vasc Biol, 2000, 20:2663-2669; Petersen et al., N Engl J Med, 2010, 362:1082-1089).

In addition to insulin, other regulators of ApoCIII gene expression have been identified. A response element for the nuclear orphan receptor rev-erb alpha has been located at positions −23 to −18 of the gene, in the ApoCIII promoter region. Rev-erb alpha decreases ApoCIII promoter activity (Raspe et al., J Lipid Res., 2002, 43, 2172-2179). The ApoCIII promoter region from positions −86 to −74 of the gene is recognized by two nuclear factors CIIIb1 and CIIIB2 (Ogami et al., J. Biol. Chem., 1991, 266, 9640-9646). ApoCIII expression is also upregulated by retinoids acting via the retinoid X receptor, and alterations in retinoid X receptor abundance affects ApoCIII transcription (Vu-Dac et al., J. Clin. Invest., 1998, 102, 625-632). Specificity protein 1 (Sp1) and hepatocyte nuclear factor-4 (HNF-4) have been shown to work synergistically to transactivate the apolipoprotein C-III promoter via the HNF-4 binding site (Kardassis et al., Biochemistry, 2002, 41, 1217-1228). HNF-4 also works in conjunction with SMAD3-SMAD4 to transactivate the ApoCIII promoter (Kardassis et al., J Biol. Chem., 2000, 275, 41405-41414).

Transgenic and knockout mice have further defined the role of ApoCIII in lipolysis. Overexpression of ApoCIII in transgenic mice leads to hypertriglyceridemia and impaired clearance of VLDL-triglycerides (de Silva et al., *J. Biol. Chem.,* 1994, 269, 2324-2335; Ito et al., *Science,* 1990, 249, 790-793). Knockout mice with a total absence of the ApoCIII protein exhibited significantly reduced plasma cholesterol and triglyceride levels compared with wild-type mice and were protected from postprandial hypertriglyceridemia (Maeda et al., *J. Biol. Chem.,* 1994, 269, 23610-23616).

Total plasma ApoCIII levels have been identified as a major determinant of serum triglycerides, and epidemiological studies have demonstrated that ApoCIII and ApoB lipoproteins that have ApoCIII as a component independently predict coronary heart disease (Sacks et al., *Circulation.* 2000. 102: 1886-1892; Lee et al., *Arterioscler Thromb Vasc Biol.* 2003. 23: 853-858). Studies also demonstrate that ApoCIII is a key determinant in the clearance of triglyceride-rich lipoproteins and its remnants in hypertriglyceridaemic states, including visceral obesity, insulin resistance and the metabolic syndrome (Mauger et al., J. Lipid Res. 2006. 47: 1212-1218; Chan et al., Clin. Chem. 2002. 278-283; Ooi et al., Clin. Sci. 2008. 114: 611-624).

Hypertriglyceridemia is a common clinical trait associated with an increased risk of cardiometabolic disease (Hegele et al. 2009, Hum Mol Genet, 18: 4189-4194; Hegele and Pollex 2009, Mol Cell Biochem, 326: 35-43) as well as of occurrence of acute pancreatitis in the most severe forms (Toskes 1990, Gastroenterol Clin North Am, 19: 783-791; Gaudet et al. 2010, Atherosclerosis Supplements, 11: 55-60; Catapano et al. 2011, Atherosclerosis, 217S: S1-S44; Tremblay et al. 2011, J Clin Lipidol, 5: 37-44). Examples of cardiometabolic disease include, but are not limited to, diabetes, metabolic syndrome/insulin resistance, and genetic disorders such as familial chylomicronemia, familial combined hyperlipidemia and familial hypertriglyceridemia.

Hypertriglyceridemia is the consequence of increased production and/or reduced or delayed catabolism of triglyceride (TG)-rich lipoproteins: VLDL and, to a lesser extent, chylomicrons (CM). Borderline high TGs (150-199 mg/dL) are commonly found in the general population and are a common component of the metabolic syndrome/insulin resistance states. The same is true for high TGs (200-499 mg/dL) except that as plasma TG levels increase, underlying genetic factors play an increasingly important etiologic role. Very high TGs (≥500 mg/dL) are most often associated with elevated CM levels as well, and are accompanied by increasing risk for acute pancreatitis. The risk of pancreatitis is considered clinically significant if TG exceeds 880 mg/dL (>10 mmol) and the European Atherosclerosis Society/European Society of Cardiology (EAS/ESC) 2011 guidelines state that actions to prevent acute pancreatitis are mandatory (Catapano et al. 2011, Atherosclerosis, 217S: S1-S44). According to the EAS/ESC 2011 guidelines, hypertriglyceridemia is the cause of approximately 10% of all cases of pancreatitis, and development of pancreatitis can occur at TG levels between 440-880 mg/dL. Based on evidence from clinical studies demonstrating that elevated TG levels are an independent risk factor for atherosclerotic CVD, the guidelines from both the National Cholesterol Education Program Adult Treatment Panel III (NCEP 2002, Circulation, 106: 3143-421) and the American Diabetes Association (ADA 2008, Diabetes Care, 31: S12-S54.) recommend a target TG level of less than 150 mg/dL to reduce cardiovascular risk.

ApoCIII-knockout mice had normal intestinal lipid absorption and hepatic VLDL triacylglycerol secretion, but a rapid clearance of VLDL triacylglycerols and VLDL cholesteryl esters from plasma that may explain the observed hypolipidaemia (Gerritsen et al., J. Lipid Res. 2005. 46: 1466-1473; Jong et al., J. Lipid Res. 2001. 42: 1578-1585). VLDL particles with ApoCIII have been cited to play a major role in identifying the high risk of coronary heart disease in hypertriglyceridemia (Campos et al., J. Lipid Res. 2001. 42: 1239-1249). A genome-wide association study found a naturally occurring ApoCIII null mutation in Lancaster Amish people demonstrated a favorable lipid profile and apparent cardioprotection, with no obvious detrimental effects (Pollin et al., *Science.* 2008. 322: 1702-1705). The mutation carriers are observed to have lower fasting and postprandial serum triglycerides and LDL-cholesterol, and higher levels of HDL-cholesterol.

The HDL class of lipoproteins comprises a heterogeneous and polydisperse population of particles that are the most dense and smallest of size (Havel and Kane. In, The Metabolic & Molecular Bases of Inherited Disease. $8^{th}$ Edition. McGraw-Hill, New York, 2001:2705-16). HDL is a macromolecular complex of lipids (cholesterol, triglycerides and phospholipids) and proteins (apolipoproteins (apo) and enzymes). The surface of HDL contains chiefly apolipoproteins A, C and E. The function of some of these apoproteins is to direct HDL from the peripheral tissues to the liver. Serum HDL levels can be affected by underlying genetic causes (Weissglas-Volkov and Pajukanta, *J Lipid Res,* 2010, 51:2032-2057)

Epidemiological studies have indicated that increased levels of HDL protect against cardiovascular disease or coronary heart disease (Gordon et al., Am. J. Med. 1977. 62: 707-714). These effects of HDL-cholesterol are independent of triglyceride and LDL-cholesterol concentrations. In clinical practice, a low plasma HDL-cholesterol is more commonly associated with other disorders that increase plasma triglycerides, for example, central obesity, insulin resistance, type 2 diabetes mellitus and renal disease (chronic renal failure or nephrotic proteinuria) (Kashyap. Am. J. Cardiol. 1998. 82: 42U-48U).

Currently, there are no known direct therapeutic agents that affect the function of ApoCIII. The hypolipidemic effect of the fibrate class of drugs has been postulated to occur via a mechanism where peroxisome proliferator activated receptor (PPAR) mediates the displacement of HNF-4 from the apolipoprotein C-III promoter, resulting in transcriptional suppression of apolipoprotein C-III (Hertz et al., *J. Biol. Chem.,* 1995, 270, 13470-13475). The statin class of hypolipidemic drugs also lower triglyceride levels via an unknown mechanism, which results in increases in lipoprotein lipase mRNA and a decrease in plasma levels of apolipoprotein C-III (Schoonjans et al., *FEBS Lett.,* 1999, 452, 160-164). Consequently, there remains a long felt need for additional agents capable of effectively inhibiting apolipoprotein C-III function.

Antisense technology is emerging as an effective means for reducing the expression of certain gene products and may therefore prove to be uniquely useful in a number of therapeutic, diagnostic, and research applications for the modulation of ApoCIII.

We have previously disclosed compositions and method for inhibiting ApoCIII by antisense compounds in US 20040208856 (U.S. Pat. No. 7,598,227), US 20060264395 (U.S. Pat. No. 7,750,141), and WO 2004/093783. In the present application, we disclose the unexpected result that antisense inhibition of ApoCIII resulted in the elevation of HDL levels and decrease in postprandial triglyceride levels. This result will be useful, for example, to treat, prevent, delay, decrease or ameliorate any one or more diseases, such as cardiovascular disease (e.g., coronary heart disease or atherogenic diseases). For example, elevated postprandial (non-fasting) triglyceride levels have been identified as a significant risk factor for cardiovascular diseases (Bansal et al., *JAMA*, 2007, 298:309-16; Nordestgaard et al., *JAMA*, 2007, 298:299-308), Also, in the present application, inhibition of ApoCIII expression unexpectedly results in increased chylomicron clearance and is therefore important in the prevention of chylomicronemia (Chait et al., 1992, *Adv Intern Med.* 1992, 37:249-73), a dyslipidemic state caused by improper clearance of chylomicron triglyceride. Severe forms of chylomicronemia can lead to pancreatitis, a life-threatening condition. By inhibiting intestinal ApoCIII, inhibition of lipoprotein lipase would be reduced, and chylomicron triglyceride clearance would be enhanced, thereby preventing pancreatitis.

SUMMARY OF THE INVENTION

Provided herein are methods of increasing HDL levels by administering to an animal a compound targeting ApoCIII.

Certain embodiments provide a method of preventing, treating, ameliorating, delaying the onset of or reducing the risk of a cardiovascular disease, disorder or condition in an animal comprising administering a compound targeting ApoCIII to the animal. The compound administered to the animal prevents, treats, ameliorates, delays the onset of, or reduces the risk of, the cardiovascular disease, disorder or condition by increasing HDL levels in the animal.

Certain embodiments provide a method of reducing the risk for a cardiovascular disease in an animal comprising administering to the animal a therapeutically effective amount of a compound comprising a modified oligonucleotide consisting of 12 to 30 linked nucleosides, wherein the modified oligonucleotide is complementary to an ApoCIII nucleic acid. In certain embodiments, the ApoCIII nucleic acid is as shown in SEQ ID NO: 1 or SEQ ID NO: 2. In certain embodiments, the compound comprises a modified oligonucleotide consisting of 12 to 30 linked nucleosides, and having a nucleobase sequence comprising at least 8 contiguous nucleobases of ISIS 304801 (SEQ ID NO: 3). In further embodiments, the compound administered to the animal reduces the risk for a cardiovascular disease, by increasing HDL levels.

Certain embodiments provide a method of preventing, treating, ameliorating or reducing at least one symptom of a cardiovascular disease in an animal, comprising administering to the animal a therapeutically effective amount of a compound comprising a modified oligonucleotide consisting of 12 to 30 linked nucleosides, wherein the modified oligonucleotide is complementary to an ApoCIII nucleic acid. In certain embodiments, the ApoCIII nucleic acid is as shown in SEQ ID NO: 1 or SEQ ID NO: 2. In certain embodiments, the compound comprises a modified oligonucleotide consisting of 12 to 30 linked nucleosides, and having a nucleobase sequence comprising at least 8 contiguous nucleobases of ISIS 304801 (SEQ ID NO: 3). In further embodiments, the compound administered to the animal prevents, treats, ameliorates or reduces at least one symptom of the cardiovascular disease in the animal, by increasing HDL levels in the animal.

Certain embodiments provide a method of raising HDL levels in an animal by administering to the animal a compound consisting of ISIS 304801 (SEQ ID NO: 3) to raise the HDL levels in the animal.

Certain embodiments provide a method of preventing, treating, ameliorating or reducing at least one symptom of a cardiovascular disease in an animal by administering to the animal a compound consisting of ISIS 304801 (SEQ ID NO: 3) to prevent, treat, ameliorate or reduce at least one symptom of the cardiovascular disease in the animal, by increasing HDL levels in the animal.

Certain embodiments provide a method of raising HDL levels in an animal by administering to the animal a modified oligonucleotide, having the sequence of SEQ ID NO: 3 (ISIS 304801) wherein the modified oligonucleotide comprises: a gap segment consisting of 10 linked deoxynucleosides; a 5' wing segment consisting of 5 linked nucleosides; a 3' wing segment consisting 5 linked nucleosides; wherein the gap segment is positioned immediately adjacent to and between the 5' wing segment and the 3' wing segment and wherein each nucleoside of each wing segment comprises a 2'-O-methyoxyethyl sugar, wherein each cytosine is a 5'-methylcytosine, and wherein each internucleoside linkage is a phosphorothioate linkage, wherein the modified oligonucleotide raises the HDL levels in the animal.

Certain embodiments provide a method of preventing, treating, ameliorating or reducing at least one symptom of a cardiovascular disease in an animal by administering to the animal a modified oligonucleotide, having the sequence of ISIS 304801 (SEQ ID NO: 3) wherein the modified oligonucleotide comprises: a gap segment consisting of 10 linked deoxynucleosides; a 5' wing segment consisting of 5 linked nucleosides; a 3' wing segment consisting 5 linked nucleosides; wherein the gap segment is positioned immediately adjacent to and between the 5' wing segment and the 3' wing segment and wherein each nucleoside of each wing segment comprises a 2'-O-methyoxyethyl sugar, wherein each cytosine is a 5'-methylcytosine, and wherein each internucleoside linkage is a phosphorothioate linkage, wherein the modified oligonucleotide prevents, treats, ameliorates or reduces at least one symptom in the animal with the cardiovascular disease by raising the HDL levels in the animal.

Certain embodiments provide a method of raising HDL levels in an animal by administering to the animal a compound comprising a modified oligonucleotide consisting of 12 to 30 linked nucleosides, wherein the modified oligonucleotide is complementary to an ApoCIII nucleic acid, as shown in SEQ ID NO: 1 or SEQ ID NO: 2, to raise the HDL levels in the animal.

Certain embodiments provide a method of preventing, treating, ameliorating or reducing at least one symptom of a cardiovascular disease in an animal by administering to the animal a compound comprising a modified oligonucleotide consisting of 12 to 30 linked nucleosides, wherein the modified oligonucleotide is complementary to an ApoCIII nucleic acid, as shown in SEQ ID NO: 1 or SEQ ID NO: 2, to preventing, treating, ameliorating or reducing at least one symptom of the cardiovascular disease in the animal, by raising the HDL levels of the animal.

Certain embodiments provide a method of decreasing CETP levels by administering a compound targeting ApoCIII to an animal. In certain embodiments, the compound comprises a modified oligonucleotide consisting of 12 to 30 linked nucleosides, and having a nucleobase sequence complementary to an ApoCIII nucleic acid. In certain embodiments, the nucleobase sequence comprises at least 8 contiguous nucleobases of ISIS 304801 (SEQ ID NO: 3). In certain embodiments, the compound consists of the nucleobases of ISIS 304801 (SEQ ID NO: 3).

Certain embodiments provide a method of increasing ApoA1, PON1, fat clearance, chylomicron triglyceride clearance, post prandial triglyceride clearance or HDL by administering a compound targeting ApoCIII to an animal. In certain embodiments, the compound comprises a modified oligonucleotide consisting of 12 to 30 linked nucleosides, and having a nucleobase sequence complementary to an ApoCIII nucleic acid. In certain embodiments, the nucleobase sequence comprises at least 8 contiguous nucleobases of ISIS 304801 (SEQ ID NO: 3). In certain embodiments, the compound consists of the nucleobases of ISIS 304801 (SEQ ID NO: 3).

Certain embodiments provide a method of preventing, delaying or ameliorating pancreatitis comprising: (a) selecting an animal with, or at risk of, pancreatitis, and (b) administering a compound targeting ApoCIII to the animal, wherein the pancreatitis is prevented, delayed or ameliorated.

Certain embodiments provide a method of preventing, delaying or ameliorating pancreatitis comprising: (a) selecting an animal with, or at risk of, pancreatiis, and (b) administering a compound targeting ApoCIII to the animal, thereby increasing chylomicron clearance, wherein the pancreatitis is prevented, delayed or ameliorated.

In certain embodiments, the animal has, or is at risk for, hypertriglyceridemia. In certain embodiments, the hypertriglyceridemia is Fredrickson Type II, IV or V. In certain embodiments, the animal has a genetic defect leading to hypertriglyceridemia. In certain embodiments, the genetic defect is a heterozygous LPL deficiency or an ApoCIII polymorphism. In certain embodiments, the animal has a triglyceride level ≥500 mg/dL and a heterozygous LPL deficiency.

In certain embodiments, the animal has a triglyceride level between 100-200 mg/dL, 100-300 mg/dL, 100-400 mg/dL, 100-500 mg/dL, 200-500 mg/dL, 300-500 mg/dL, 400-500 mg/dL, 500-1000 mg/dL, 600-1000 mg/dL, 700-1000 mg/dL, 800-1000 mg/dL, 900-1000 mg/dL, 500-1500 mg/dL, 1000-1500 mg/dL, 100-2000 mg/dL, 150-2000 mg/dL, 200-2000 mg/dL, 300-2000 mg/dL, 400-2000 mg/dL, 500-2000 mg/dL, 600-2000 mg/dL, 700-2000 mg/dL, 800-2000 mg/dL, 900-2000 mg/dL, 1000-2000 mg/dL, 1100-2000 mg/dL, 1200-2000 mg/dL, 1300-2000 mg/dL, 1400-2000 mg/dL, or 1500-2000 mg/dL.

In certain embodiments, increased chylomicron clearance enhances clearance of postprandial triglycerides and/or decreases postprandial triglycerides.

Certain embodiments provide a use of a compound targeted to ApoCIII for preventing, treating, ameliorating or reducing at least one symptom of a cardiovascular disease, by increasing HDL levels.

Certain embodiments provide a use of a compound targeted to ApoCIII for increasing HDL levels in an animal.

Certain embodiments provide a use of a compound targeted to ApoCIII for the preparation of a medicament for increasing HDL levels in an animal.

Certain embodiments provide a use of a compound targeted to ApoCIII for the preparation of a medicament for improving the ratio of TG to HDL.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE, 2'-O(CH$_2$)$_2$—OCH$_3$ and 2'-O-(2-methoxyethyl)) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to ApoCIII is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Agent" means an active substance that can provide a therapeutic benefit when administered to an animal. "First Agent" means a therapeutic compound of the invention. For example, a first agent can be an antisense oligonucleotide targeting ApoCIII. "Second agent" means a second therapeutic compound of the invention (e.g. a second antisense oligonucleotide targeting ApoCIII) and/or a non-ApoCIII therapeutic compound.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. As used herein, the term "antisense compound" encompasses pharmaceutically acceptable derivatives of the compounds described herein.

"Antisense inhibition" means the reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid. As used herein, the term "antisense oligonucleotide" encompasses pharmaceutically acceptable derivatives of the compounds described herein.

"ApoCIII" means any nucleic acid or protein sequence encoding ApoCIII. For example, in certain embodiments, an ApoCIII includes a DNA sequence encoding ApoCIII, a RNA sequence transcribed from DNA encoding ApoCIII (including genomic DNA comprising introns and exons), a mRNA sequence encoding ApoCIII, or a peptide sequence encoding ApoCIII.

"ApoCIII mRNA" means a mRNA encoding an ApoCIII protein.

"ApoCIII protein" means any protein sequence encoding ApoCIII.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, hypertriglyceridemia and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-estrified cholesterol present in the plasma or serum.

"Cholesterol absorption inhibitor" means an agent that inhibits the absorption of exogenous cholesterol obtained from diet.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid. In certain embodiments, complementarity between the first and second nucleic acid can be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Contiguous nucleobases" means nucleobases immediately adjacent to each other.

"Constrained ethyl" or "cEt" refers to a bicyclic nucleoside having a furanosyl sugar that comprises a methyl(methyleneoxy) (4'-CH($CH_3$)—O-2') bridge between the 4' and the 2' carbon atoms.

"Cross-reactive" means an oligomeric compound targeting one nucleic acid sequence can hybridize to a different nucleic acid sequence. For example, in some instances an antisense oligonucleotide targeting human ApoCIII can cross-react with a murine ApoCIII. Whether an oligomeric compound cross-reacts with a nucleic acid sequence other than its designated target depends on the degree of complementarity the compound has with the non-target nucleic acid sequence. The higher the complementarity between the oligomeric compound and the non-target nucleic acid, the more likely the oligomeric compound will cross-react with the nucleic acid.

"Cure" means a method that restores health or a prescribed treatment for an illness.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition may be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as chylomicron, cholesterol and triglycerides as well as lipoproteins such as low-density lipoprotein (LDL) cholesterol. An example of a dyslipidemia is chylomicronemia.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

The "Fredrickson" system is used to classify primary (genetic) causes of dislipidemia into several subgroups or types. Dislipidemia types that may be amenable to therapy with the compounds disclosed herein include, but are not limited to, Fredrickson Type II, IV and V.

"Fredrickson Type I" exists in several forms: Type 1a is a lipoprotein lipase deficiency due to a deficiency of LPL or altered apoC-II; Type Ib is a familial apoprotein CII deficiency, a condition caused by a lack of lipoprotein lipase activator; and Type Ic is a chylomicronemia due to circulating inhibitor of lipoprotein lipase. Type I is a rare disorder that usually presents in childhood. It is characterized by severe elevations in chylomicrons and extremely elevated TG levels (always reaching well above 1000 mg/dL and not infrequently rising as high as 10,000 mg/dL or more) with episodes of abdominal pain, recurrent acute pancreatitis, eruptive cutaneous xanthomata, and hepatosplenomegaly. Patients rarely develop atherosclerosis, perhaps because their plasma lipoprotein particles are too large to enter into the arterial intima (Nordestgaard et al., J Lipid Res, 1988, 29:1491-1500; Nordestgaard et al., Arteriosclerosis, 1988, 8:421-428). Type I is usually caused by mutations of either the LPL gene, or of the gene's cofactor apoC-II, resulting in the inability of affected individuals to produce functionally active LPL. Patients are either homozygous for such mutations or compound heterozygous. The prevalence is approximately 1 in 1,000,000 in the general population and much higher in South Africa and Eastern Quebec as a result of a founder effect. Patients respond minimally, or not at all, to TG-lowering drugs (Tremblay et al., J Clin Lipidol, 2011, 5:37-44; Brisson et al., Pharmacogenet Genom, 2010, 20:742-747) and hence restriction of dietary fat to 20 grams/day or less is used to manage the symptoms of this rare disorder.

"Fredrickson Type II" is the most common form of primary hyperlipidemia. It is further classified into Type IIa and Type IIb, depending mainly on whether there is elevation in VLDL in addition to LDL cholesterol (LDL-C). Type IIa (familial hypercholesterolemia) may be sporadic (due to dietary factors), polygenic, or truly familial as a result of a mutation in either the LDL receptor gene on chromosome 19 (0.2% of the population) or the apolipoprotein B (apoB) gene (0.2%). The familial form is characterized by tendon xanthoma, xanthelasma and premature cardiovascular disease. The incidence of this disease is about 1 in 500 for heterozygotes, and 1 in 1,000,000 for homozygotes. Type IIb (also known as familial combined hyperlipoproteinemia) is a mixed hyperlipidemia (high cholesterol and TG levels), caused by elevations in LDL-C and in VLDL. The high VLDL levels are due to overproduction of substrates, including TG, acetyl CoA, and an increase in B-100 synthesis. They may also be caused by the decreased clearance of LDL. Prevalence in the population is about 10%.

"Fredrickson Type III" (also known as dysbetalipoproteinemia) is a remnant removal disease, or broad-beta disease (Fern et al., J Clin Pathol, 2008, 61:1174-118). It is due to cholesterol-rich VLDL (β-VLDL). Typically, patients with this condition have elevated plasma cholesterol and TG levels because of impaired clearance of chylomicron and VLDL remnants (e.g. IDL). The impaired clearance is due to a defect in apolipoprotein E (apoE). Normally functioning apoE contained on the remnants would enable binding to the LDL receptor and removal from the circulation. Accumulation of the remnants in affected individuals can result in xanthomatosis and premature coronary and/or peripheral vascular disease. The most common cause for Type III is the presence of apoE E2/E2 genotype. Its prevalence has been estimated to be approximately 1 in 10,000.

"Fredrickson Type IV" (also known as familial hypertriglyceridemia) is an autosomal dominant condition occurring in approximately 1% of the population. TG levels are elevated as a result of excess hepatic production of VLDL or heterozygous LPL deficiency, but are almost always less than 1000 mg/dL. Serum cholesterol levels are usually within normal limits. The disorder is heterogeneous and the phenotype strongly influenced by environmental factors, particularly carbohydrate and ethanol consumption.

"Fredrickson Type V" has high VLDL and chylomicrons. It is characterized by carriers of loss-of-function LPL gene variants associated with LPL activity of at least 20% (i.e. partial LPL deficiency as compared to Fredrickson Type I). These patients present with lactescent plasma and severe hypertriglyceridemia because of chylomicrons and VLDL. TG levels are invariably greater than 1000 mg/dL and total cholesterol levels are always elevated. The LDL-C level is usually low. It is also associated with increased risk for acute pancreatitis, glucose intolerance and hyperuricemia. Symptoms generally present in adulthood (>35 years) and, although the prevalence is relatively rare, it is much more common than homozygous or compound heterozygous LPL deficient patients.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" or "gap segment" and the external regions may be referred to as "wings" or "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"High density lipoprotein-C (HDL-C)" means cholesterol associated with high density lipoprotein particles. Concentration of HDL-C in serum (or plasma) is typically quantified in mg/dL or nmol/L. "HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

"Hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ*, 2007, 176:1113-1120).

"Identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Immediately adjacent" means there are no intervening elements between the immediately adjacent elements, for example, between regions, segments, nucleotides and/or nucleosides.

"Increasing HDL" or "raising HDL" means increasing the level of HDL in an animal after administration of at least one compound of the invention, compared to the HDL level in an animal not administered any compound.

"Individual" or "subject" or "animal" means a human or non-human animal selected for treatment or therapy.

"Induce", "inhibit", "potentiate", "elevate", "increase", "decrease", "reduce" or the like denote quantitative differences between two states. For example, "an amount effective to inhibit the activity or expression of ApoCIII" means that the level of activity or expression of ApoCIII in a treated sample will differ from the level of ApoCIII activity or expression in an untreated sample. Such terms are applied to, for example, levels of expression, and levels of activity.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids in a subject. "Lipid-raising" means an increase in a lipid (e.g., HDL) in a subject. Lipid-lowering or lipid-raising can occur with one or more doses over time.

"Lipid-lowering therapy" or "lipid lowering agent" means a therapeutic regimen provided to a subject to reduce one or more lipids in a subject. In certain embodiments, a lipid-lowering therapy is provided to reduce one or more of CETP, ApoB, total cholesterol, LDL-C, VLDL-C, IDL-C, non-HDL-C, triglycerides, small dense LDL particles, and Lp(a) in a subject. Examples of lipid-lowering therapy include statins, fibrates, MTP inhibitors.

"Lipoprotein", such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond. For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the oligonucleotide and the target nucleic acid are considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base, and not necessarily the linkage at one or more positions of an oligomeric compound; for example nucleoside mimetics having morpholino, cyclohexenyl, cyclohexyl, tetrahydropyranyl, bicyclo or tricyclo sugar mimetics such as non-furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(C=O)—O— or other non-phosphodiester linkage).

"Oligomeric compound" or "oligomer" means a polymer of linked monomeric subunits which is capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent from one another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to ApoCIII is pharmaceutical agent.

"Pharmaceutical composition" or "composition" means a mixture of substances suitable for administering to an individual. For example, a pharmaceutical composition may comprise one or more active agents and a pharmaceutical carrier, such as a sterile aqueous solution.

"Pharmaceutically acceptable carrier" means a medium or diluent that does not interfere with the structure of the compound. Certain of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

"Pharmaceutically acceptable derivative" or "salts" encompasses derivatives of the compounds described herein such as solvates, hydrates, esters, prodrugs, polymorphs, isomers, isotopically labelled variants, pharmaceutically acceptable salts and other derivatives known in the art.

"Pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases.

"Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form (i.e., a drug) within the body or cells thereof by the action of endogenous enzymes or other chemicals or conditions.

"Raise" means to increase in amount. For example, to raise plasma HDL levels means to increase the amount of HDL in the plasma.

"Ratio of TG to HDL" means the TG levels relative to HDL levels. The occurrence of high TG and/or low HDL has been linked to cardiovascular disease incidence, outcomes and mortality. "Improving the ratio of TG to HDL" means to decrease TG and/or raise HDL levels.

"Reduce" means to bring down to a smaller extent, size, amount, or number. For example, to reduce plasma triglyceride levels means to bring down the amount of triglyceride in the plasma.

"Region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region.

The structurally defined regions for ApoCIII can be obtained by accession number from sequence databases such as NCBI and such information is incorporated herein by reference. In certain embodiments, a target region may encompass the sequence from a 5' target site of one target segment within the target region to a 3' target site of another target segment within the target region.

"Ribonucleotide" means a nucleotide having a hydroxy at the 2' position of the sugar portion of the nucleotide. Ribonucleotides can be modified with any of a variety of substituents.

"Second agent" or "second therapeutic agent" means an agent that can be used in combination with a "first agent". A second therapeutic agent can include, but is not limited to, an siRNA or antisense oligonucleotide including antisense oligonucleotides targeting ApoCIII. A second agent can also include anti-ApoCIII antibodies, ApoCIII peptide inhibitors, cholesterol lowering agents, lipid lowering agents, glucose lowering agents and anti-inflammatory agents.

"Segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment.

"Shortened" or "truncated" versions of antisense oligonucleotides or target nucleic acids taught herein have one, two or more nucleosides deleted.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity to a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Subject" means a human or non-human animal selected for treatment or therapy.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Treat" refers to administering a compound of the invention to effect an alteration or improvement of a disease, disorder, or condition.

"Triglyceride" or "TG" means a lipid or neutral fat consisting of glycerol combined with three fatty acid molecules.

"Type 2 diabetes," (also known as "type 2 diabetes mellitus", "diabetes mellitus, type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means one or a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide a method of reducing ApoCIII levels in an animal by administering a compound to the animal targeting ApoCIII, thereby decreasing ApoCIII levels. In certain embodiments, ApoCIII levels are reduced in the liver or small intestine.

Certain embodiments provide a method of increasing HDL levels and/or improving the ratio of TG to HDL in an animal by administering a compound to the animal wherein the compound targets ApoCIII and increases HDL levels and/or improves the ratio of TG to HDL.

Certain embodiments provide a method of preventing, delaying or ameliorating a cardiovascular disease, disorder, condition, or symptom thereof, in an animal comprising administering a compound targeting ApoCIII to the animal, wherein the compound administered to the animal prevents, treats or ameliorates the cardiovascular disease, disorder, condition or symptom in the animal by increasing HDL levels in the animal and/or improving the ratio of TG to HDL.

Certain embodiments provide a method of preventing, delaying or ameliorating a pancreatitis in an animal comprising administering a compound targeting ApoCIII to the animal, wherein the compound administered to the animal prevents, treats or ameliorates the pancreatitis in the animal by increasing HDL levels in the animal and/or improving the ratio of TG to HDL. In certain embodiments, the pancreatitis is acute pancreatitis.

Certain embodiments provide a method of preventing, treating, ameliorating, delaying the onset, or reducing the risk of, a cardiovascular disease, disorder or condition in an animal, comprising of administering to the animal a compound that targets ApoCIII, wherein the compound prevents, treats, ameliorates, delays the onset, or reduces of the risk of the cardiovascular disease, disorder or condition in the animal by increasing HDL levels in the animal and/or improving the ratio of TG to HDL.

Certain embodiments provide a method of decreasing CETP levels by administering a compound targeting ApoCIII to an animal.

Certain embodiments provide a method of increasing ApoA1, PON1, fat clearance, chylomicron triglyceride clearance and/or HDL by administering a compound targeting ApoCIII to an animal. Certain embodiments provide a method for improving the ratio of TG to HDL.

In certain embodiments, the ApoCIII nucleic acid is any of the sequences set forth in GENBANK Accession No. NM_000040.1 (incorporated herein as SEQ ID NO: 1), and GENBANK Accession No. NT_033899.8 truncated from nucleotides 20262640 to 20266603 (incorporated herein as SEQ ID NO: 2).

In certain embodiments, the compound targeting ApoCIII is a modified oligonucleotide. In further embodiments, the modified oligonucleotide has a nucleobase sequence comprising at least 8 contiguous nucleobases of ISIS 304801 (SEQ ID NO: 3). In certain embodiments, the modified oligonucleotide is at least 80%, at least 85%, at least 90%, at least 95%, at least 98% or at least 100% complementary to SEQ ID NO: 1 or SEQ ID NO: 2.

In certain embodiments, the modified oligonucleotide consists of a single-stranded modified oligonucleotide.

In certain embodiments, the modified oligonucleotide consists of 12-30 linked nucleosides.

In certain embodiments, the modified oligonucleotide consists of 20 linked nucleosides.

In certain embodiments, the compound comprises at least one modified internucleoside linkage. In certain embodiments, the internucleoside linkage is a phosphorothioate internucleoside linkage.

In certain embodiments, the compound comprises at least one nucleoside comprising a modified sugar. In certain embodiments, the at least one modified sugar is a bicyclic sugar. In certain embodiments, the at least one modified sugar comprises a 2'-O-methoxyethyl.

In certain embodiments, the compound comprises at least one nucleoside comprising a modified nucleobase. In certain embodiments, the modified nucleobase is a 5-methylcytosine.

In certain embodiments, the compound comprising modified oligonucleotide comprises: (i) a gap segment consisting of linked deoxynucleosides; (ii) a 5' wing segment consisting of linked nucleosides; (iii) a 3' wing segment consisting of linked nucleosides, wherein the gap segment is positioned immediately adjacent to and between the 5' wing segment and the 3' wing segment and wherein each nucleoside of each wing segment comprises a modified sugar.

In certain embodiments, the compound comprising modified oligonucleotide comprises: (i) a gap segment consisting of 8-12 linked deoxynucleosides; (ii) a 5' wing segment consisting of 1-5 linked nucleosides; (iii) a 3' wing segment consisting of 1-5 linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5'-methylcytosine, and wherein each internucleoside linkage is a phosphorothioate linkage.

In certain embodiments, the compound comprising modified oligonucleotide comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5'-methylcytosine, and wherein each internucleoside linkage is a phosphorothioate linkage.

In certain embodiments, the modified oligonucleotide has a nucleobase sequence comprising at least 8 contiguous nucleobases of a nucleobase sequence of ISIS 304801 (SEQ ID NO: 3).

Certain embodiments provide a method of reducing the risk of a cardiovascular disease in an animal by administering to the animal a therapeutically effective amount of a compound comprising a modified oligonucleotide consisting of 12 to 30 linked nucleosides, wherein the modified oligonucleotide is complementary to an ApoCIII nucleic acid and wherein the modified oligonucleotide increases HDL levels and/or improves the ratio of TG to HDL. In certain embodiments, the ApoCIII nucleic acid is either SEQ ID NO: 1 or SEQ ID NO: 2. In certain embodiments, the modified oligonucleotide is at least 80%, at least 85%, at least 90%, at least 95%, at least 98% or at least 100% complementary to SEQ ID NO: 1 or SEQ ID NO: 2. In further embodiments the modified nucleotide comprises at least 8 contiguous nucleobases of the nucleobase sequence of ISIS 304801 (SEQ ID NO: 3).

Certain embodiments provide a method of preventing, treating, ameliorating, or reducing at least one symptom of a cardiovascular disease in an animal, comprising administering to the animal a therapeutically effective amount of a compound comprising a modified oligonucleotide consisting of 12 to 30 linked nucleosides and is complementary to an ApoCIII nucleic acid. In certain embodiments, the ApoCIII nucleic acid is either SEQ ID NO: 1 or SEQ ID NO: 2. In certain embodiments, the modified oligonucleotide is at least 80%, at least 85%, at least 90%, at least 95%, at least 98% or at least 100% complementary to SEQ ID NO: 1 or SEQ ID NO: 2. In further embodiments, the compound administered to the animal prevents, treats, ameliorates or reduces at least one symptom of the cardiovascular disease by increasing HDL levels and/or improving the ratio of TG to HDL. In further embodiments, the modified oligonucleotide comprises at least 8 contiguous nucleobases of ISIS 304801 (SEQ ID NO: 3).

In further embodiments, symptoms of a cardiovascular disease include, but are not limited to, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Certain embodiments provide a method of raising HDL levels and/or improving the ratio of TG to HDL in an animal by administering to the animal a compound consisting of the nucleobase sequence of ISIS 304801 (SEQ ID NO: 3). Further embodiments provide a method of preventing, treating, ameliorating or reducing at least one symptom of a cardiovascular disease in an animal by administering to the animal a compound consisting of the nucleobase sequence of ISIS 304801 (SEQ ID NO: 3), thereby increasing the HDL levels and/or improving the ratio of TG to HDL in the animal.

Certain embodiments provide a method of raising HDL levels and/or improving the ratio of TG to HDL in an animal by administering to the animal a modified oligonucleotide having the sequence of ISIS 304801, wherein the modified oligonucleotide comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5'-methylcytosine, and wherein each internucleoside linkage is a phosphorothioate linkage.

Certain embodiments provide a method of preventing, treating, ameliorating, or reducing at least one symptom of a cardiovascular disease in an animal by administering to the animal a modified oligonucleotide having the sequence of ISIS 304801 (SEQ ID NO: 3), wherein the modified oligonucleotide of the compound comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar, wherein each cytosine is a 5'-methylcytosine, and wherein each internucleoside linkage is a phosphorothioate linkage.

Certain embodiments provide a method of raising the HDL levels and/or improving the ratio of TG to HDL in an animal by administering to the animal a compound comprising a modified oligonucleotide consisting of 12 to 30 linked nucleosides, wherein the modified oligonucleotide is complementary to an ApoCIII nucleic acid. In certain embodiments, the ApoCIII nucleic acid is either SEQ ID NO: 1 or SEQ ID NO: 2. In certain embodiments, the modified oligonucleotide is at least 80%, at least 85%, at least 90%, at least 95%, at least 98% or at least 100% complementary to SEQ ID NO: 1 or SEQ ID NO: 2.

Certain embodiments provide a method of preventing, treating, ameliorating or reducing at least one symptom of a cardiovascular disease in an animal by administering to the animal a compound comprising a modified oligonucleotide consisting of 12 to 30 linked nucleosides, wherein the modified oligonucleotide is complementary to an ApoCIII nucleic acid, and raises the HDL levels in the animal. In certain embodiments, the ApoCIII nucleic acid is either SEQ ID NO: 1 or SEQ ID NO: 2. In certain embodiments, the modified oligonucleotide is at least 80%, at least 85%, at least 90%, at least 95%, at least 98% or at least 100% complementary to SEQ ID NO: 1 or SEQ ID NO: 2.

Certain embodiments provide a method of decreasing CETP levels by administering a compound targeting ApoCIII to an animal. In certain embodiments, the compound comprises a modified oligonucleotide consisting of 12 to 30 linked nucleosides, wherein the modified oligonucleotide is complementary to an ApoCIII nucleic acid. In certain embodiments, the ApoCIII nucleic acid is either SEQ ID NO: 1 or SEQ ID NO: 2. In certain embodiments, the modified oligonucleotide is at least 80%, at least 85%, at least 90%, at least 95%, at least 98% or at least 100% complementary to SEQ ID NO: 1 or SEQ ID NO: 2. In certain embodiments, the compound comprises a modified oligonucleotide consisting of 12 to 30 linked nucleosides and has a nucleobase sequence comprising at least 8 contiguous nucleobases of ISIS 304801 (SEQ ID NO: 3). In certain embodiments, the compound consists of the nucleobases of ISIS 304801 (SEQ ID NO: 3).

Certain embodiments provide a method of increasing ApoA1, PON1, fat clearance, chylomicron triglyceride clearance and/or HDL by administering a compound targeting ApoCIII to an animal. In certain embodiments, the compound comprises a modified oligonucleotide consisting of 12 to 30 linked nucleosides, wherein the modified oligonucleotide is complementary to an ApoCIII nucleic acid. In certain embodiments, the ApoCIII nucleic acid is either SEQ ID NO: 1 or SEQ ID NO: 2. In certain embodiments, the modified oligonucleotide is at least 80%, at least 85%, at least 90%, at least 95%, at least 98% or at least 100% complementary to SEQ ID NO: 1 or SEQ ID NO: 2. In certain embodiments, the compound comprises a modified oligonucleotide consisting of 12 to 30 linked nucleosides and has a nucleobase sequence comprising at least 8 contiguous nucleobases of ISIS 304801 (SEQ ID NO: 3). In certain embodiments, the compound consists of the nucleobases of ISIS 304801 (SEQ ID NO: 3).

In certain embodiments, the animal is human.

In certain embodiments, the cardiovascular disease is aneurysm, angina, arrhythmia, atherosclerosis, cerebrovascular disease, coronary heart disease, hypertension, dyslipidemia, hyperlipidemia, hypertriglyceridemia or hypercholesterolemia. In certain embodiments, the dyslipidemia is chylomicronemia.

In certain embodiments, the animal is at risk for pancreatitis. In certain embodiments, reducing ApoCIII levels in the liver and/or small intestine prevents pancreatitis. In certain embodiments, raising HDL levels and/or improving the ratio of TG to HDL prevents pancreatitis.

In certain embodiments, reducing ApoCIII levels in the liver and/or small intestine enhance clearance of postprandial triglyceride. In certain embodiments, raising HDL levels and/or improving the ratio of TG to HDL enhance clearance of postprandial triglyceride. In certain embodiments, reducing ApoCIII levels in the liver and/or small intestine lowers postprandial triglyceride. In certain embodiments, raising HDL levels and/or improving the ratio of TG to HDL lowers postprandial triglyceride.

In certain embodiments, reducing ApoCIII levels in the liver and/or small intestine improves the ratio of HDL to TG.

In certain embodiments, the compound is parenterally administered. In further embodiments, the parenteral administration is subcutaneous.

In certain embodiments, the compound is co-administered with a second agent. In certain embodiments, the second agent is a glucose-lowering agent. In certain embodiments, the second agent is an LDL, TG or cholesterol lowering agent.

In certain embodiments, the compound and the second agent are administered concomitantly or sequentially.

In certain embodiments, the compound is a salt form. In further embodiments, the compound further comprises of a pharmaceutically acceptable carrier or diluent.

Certain embodiments provide use of a compound targeted to ApoCIII in the preparation of a medicament for decreasing ApoCIII levels in an animal. Certain embodiments provide use of a compound targeted to ApoCIII for decreasing ApoCIII levels in an animal. In certain embodiments, ApoCIII levels are decreased in the liver or small intestine. Certain embodiments provide use of a compound targeted to ApoCIII in the preparation of a medicament for preventing, treating, ameliorating or reducing at least one symptom of a cardiovascular disease by increasing HDL levels and/or improving the ratio of TG to HDL. Certain embodiments provide use of a compound targeted to ApoCIII for preventing, treating, ameliorating or reducing at least one symptom of a cardiovascular disease by increasing HDL levels and/or improving the ratio of TG to HDL. Certain embodiments provide a use of a compound targeted to ApoCIII for increasing HDL levels and/or improving the ratio of TG to HDL in an animal. Certain embodiments provide a use of a compound targeted to ApoCIII for the preparation of a medicament for increasing HDL levels and/or improving the ratio of TG to HDL in an animal. In certain embodiments, the compound is at least 80%, at least 85%, at least 90%, at least 95%, at least 98% or at least 100% complementary to an ApoCIII nucleic acid sequence. In certain embodiments, the ApoCIII nucleic acid is either SEQ ID NO: 1 or SEQ ID NO: 2. In certain embodiments, the compound is a modified oligonucleotide. In certain embodiments, the modified oligonucleotide has a nucleobase sequence comprising at least 8 nucleobases of ISIS 304801 (SEQ ID NO: 3). In certain embodiments, the modified oligonucleotide has the nucleobase sequence of ISIS 304801 (SEQ ID NO: 3). Certain embodiments provide use of a compound targeted to ApoCIII in the preparation of a medicament for treating an animal with pancreatitis or at risk for pancreatitis. Certain embodiments provide use of a compound targeted to ApoCIII for treating an animal with pancreatitis or at risk for pancreatitis. Certain embodiments provide use of a compound targeted to ApoCIII in the preparation of a medicament for reducing ApoCIII levels in the liver and/or small intestine. Certain embodiments provide use of a compound targeted to ApoCIII for reducing ApoCIII levels in the liver and/or small intestine. Certain embodiments provide use of a compound targeted to ApoCIII in the preparation of a medicament for preventing pancreatitis. Certain embodiments provide use of a compound targeted to ApoCIII for preventing pancreatitis.

Certain embodiments provide use of a compound targeted to ApoCIII in the preparation of a medicament for reducing ApoCIII levels in the liver and/or small intestine in an animal with hypertriglyceridemia. Certain embodiments provide use of a compound targeted to ApoCIII for reducing ApoCIII levels in the liver and/or small intestine in an animal with hypertriglyceridemia. Certain embodiments provide use of a compound targeted to ApoCIII in the preparation of a medicament for enhancing clearance of postprandial triglyceride. Certain embodiments provide use of a compound targeted to ApoCIII for enhancing clearance of postprandial triglyceride. Certain embodiments provide use of a compound targeted to ApoCIII in the preparation of a medicament for lowering postprandial triglyceride. Certain embodiments provide use of a compound targeted to ApoCIII for lowering postprandial triglyceride.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an ApoCIII nucleic acid is 12 to 30 nucleotides in length. In other words, antisense compounds are from 12 to 30 linked nucleobases. In other embodiments, the antisense compound comprises a modified oligonucleotide consisting of 8 to 80, 10 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In some embodiments, the antisense compound is an antisense oligonucleotide.

In certain embodiments, the antisense compound comprises a shortened or truncated modified oligonucleotide. The shortened or truncated modified oligonucleotide can have one or more nucleosides deleted from the 5' end (5' truncation), one or more nucleosides deleted from the 3' end (3' truncation) or one or more nucleosides deleted from the central portion. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the central portion, 5' or 3' end of the oligonucleotide. When two or more additional nucleosides are present, the added nucleosides may be adjacent to each other, for example, in an oligonucleotide having two nucleosides added to the central portion, to the 5' end (5' addition), or alternatively to the 3' end (3' addition), of the oligonucleotide. Alternatively, the added nucleosides may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an ApoCIII nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA: DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 1-8-1, 2-6-2, 2-13-2, 1-8-2, 2-8-3, 3-10-2, 1-18-2 or 2-18-2.

In certain embodiments, the antisense compound as a "wingmer" motif, having a wing-gap or gap-wing configuration, i.e. an X—Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13 or 5-13.

In certain embodiments, antisense compounds targeted to an ApoCIII nucleic acid possess a 5-10-5 gapmer motif.

In certain embodiments, an antisense compound targeted to an ApoCIII nucleic acid has a gap-widened motif.

Target Nucleic Acids, Target Regions and Nucleotide Sequences

Nucleotide sequences that encode ApoCIII include, without limitation, the following: GENBANK Accession No. NM_000040.1 (incorporated herein as SEQ ID NO: 1), and GENBANK Accession No. NT_033899.8 truncated from nucleotides 20262640 to 20266603 (incorporated herein as SEQ ID NO: 2).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for ApoCIII can be obtained by accession number from sequence databases such as NCBI and such information is incorporated herein by reference. In certain embodiments, a target region may encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compounds are targeted. "5' target site" refers to the 5'-most nucleotide of a target segment. "3' target site" refers to the 3'-most nucleotide of a target segment.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed, herein.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in ApoCIII mRNA levels are indicative of inhibition of ApoCIII expression. Reductions in levels of an ApoCIII protein can be indicative of inhibition of target mRNA expression. Further, phenotypic changes can be indicative of inhibition of ApoCIII expression. For example, an increase in HDL levels, decrease in LDL levels, or decrease in triglyceride levels, are among phenotypic changes that may be assayed for inhibition of ApoCIII expression. Other phenotypic indications, e.g., symptoms associated with a cardiovascular disease, may also be assessed; for example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Hybridization

In some embodiments, hybridization occurs between an antisense compound disclosed herein and an ApoCIII nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, 3$^{rd}$ Ed., 2001). In certain embodiments, the antisense compounds provided herein are specifically hybridizable with an ApoCIII nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an ApoCIII nucleic acid).

An antisense compound may hybridize over one or more segments of an ApoCIII nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an ApoCIII nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In certain embodiments, the antisense compounds provided herein, or specified portions thereof, are fully complementary (i.e. 100% complementary) to a target nucleic acid, or specified portion thereof. For example, an antisense compound may be fully complementary to an ApoCIII nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase(s) can be at the 5' end or 3' end of the antisense compound. Alternatively, the non-complementary nucleobase(s) can be at an internal position of the antisense compound. When two or more non-complementary nucleobases are present, they can be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an ApoCIII nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an ApoCIII nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 10 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or sequence of a compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an ApoCIII nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(C=O)—N(R$_m$)(R$_n$), and O—CH$_2$—C(C=O)—N(R$_1$)—(CH$_2$)$_2$—N(R$_m$)(R$_n$), where each R$_l$, R$_m$ and R$_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, $C_1$-$C_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Serial Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(C=O)—, —C(=N$R_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-(CH$_2$)$_2$-2', 4'-(CH$_2$)$_3$-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

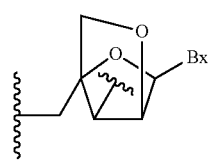

(A)

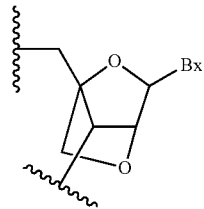

(B)

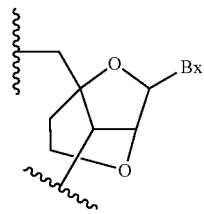

(C)

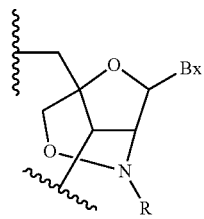

(D)

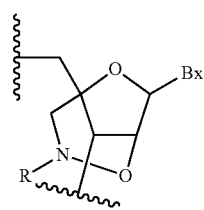

(E)

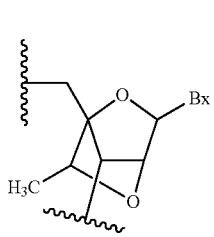

(F)

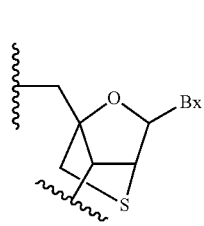

(G)

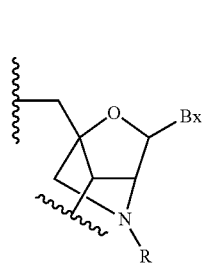

(H)

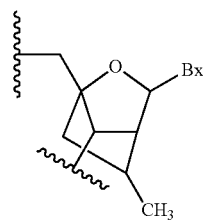

(I)

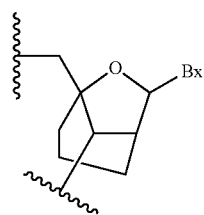

(J)

wherein Bx is the base moiety and R is independently H, a protecting group or $C_1$-$C_{12}$ alkyl.

In certain embodiments, bicyclic nucleosides are provided having Formula I:

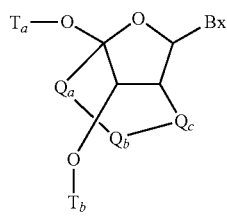

I wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

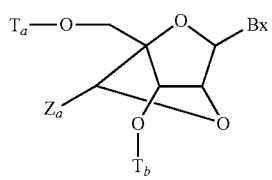

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

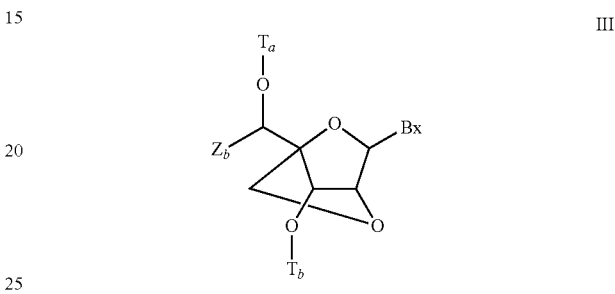

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

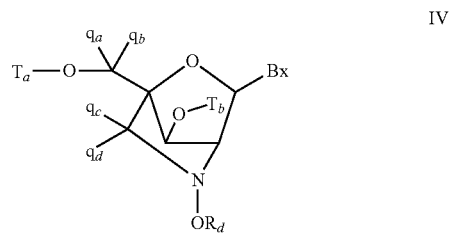

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

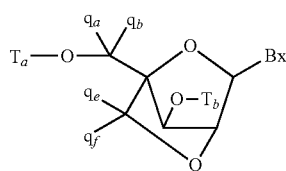

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

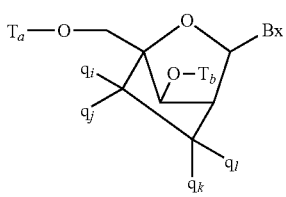

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

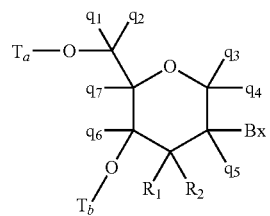

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif. In certain embodiments, the modified sugar moiety is a cEt. In certain embodiments, the cEt modified nucleotides are arranged throughout the wings of a gapmer motif Modified Nucleobases Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine.

Heterocyclic base moieties may include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an ApoCIII nucleic acid comprise one or more modified nucleobases. In certain embodiments, gap-widened antisense oligonucleotides targeted to an ApoCIII nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an ApoCIII nucleic acid can be utilized in pharmaceutical compositions by combining the antisense compound with a suitable pharmaceutically acceptable diluent or carrier.

In certain embodiments, the "pharmaceutical carrier" or "excipient" is a pharmaceutically acceptable solvent, suspending agent or any other pharmacologically inert vehicle for delivering one or more nucleic acids to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acids, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an ApoCIII nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or an oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of ApoCIII nucleic acids or proteins can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrooke and Russell in *Molecular Cloning. A Laboratory Manual*. Third Edition. Cold Spring Harbor Laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrooke and Russell in *Molecular Cloning. A Laboratory Manual*. Third Edition. Cold Spring Harbor Laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrooke and Russell in *Molecular Cloning. A Laboratory Manual*. Third Edition. Cold Spring Harbor Laboratory Press, Cold Spring Harbor, N.Y. 2001). Antisense oligonucleotides are typically used at concentrations ranging from 1 nM to 300 nM when transfected with LIPOFECTAMINE2000® (Invitrogen, Carlsbad, Calif.), Lipofectin® (Invitrogen, Carlsbad, Calif.) or Cytofectin™ (Genlantis, San Diego, Calif.). Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art (Sambrooke and Russell in *Molecular Cloning. A Laboratory Manual*. Third Edition. Cold Spring Harbor Laboratory Press, Cold Spring Harbor, N.Y. 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an ApoCIII nucleic acid can be assayed in a variety of ways known in the art (Sambrooke and Russell in *Molecular Cloning. A Laboratory Manual*. Third Edition. Cold Spring Harbor Laboratory Press, Cold Spring Harbor, N.Y. 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems, Foster City, Calif.) is used to measure RIBOGREEN® fluorescence.

Probes and primers are designed to hybridize to an ApoCIII nucleic acid. Methods for designing real-time PCR probes and primers are well known in the art, and may include the use of software such as PRIMER EXPRESS® Software (Applied Biosystems, Foster City, Calif.).

Gene target quantities obtained by RT, real-time PCR can use either the expression level of GAPDH or Cyclophilin A, genes whose expression are constant, or by quantifying total RNA using RiboGreen™ (Molecular Probes, Inc. Eugene, Oreg.). GAPDH or Cyclophilin A expression can be quantified by RT, real-time PCR, by being run simultaneously with the target, multiplexing, or separately. Total RNA was quantified using RiboGreen™ RNA quantification reagent (Molecular Probes, Inc. Eugene, Oreg.).

Analysis of Protein Levels

Antisense inhibition of ApoCIII nucleic acids can be assessed by measuring ApoCIII protein levels. Protein levels of ApoCIII can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrooke and Russell in *Molecular Cloning. A Laboratory Manual*. Third Edition. Cold Spring Harbor Laboratory Press, Cold Spring Harbor, N.Y. 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and mouse ApoCIII are commercially available.

In Vivo Testing of Antisense Compounds

Antisense compounds, for example, antisense oligonucleotides, are tested in animals to assess their ability to inhibit expression of ApoCIII and produce phenotypic changes. Testing can be performed in normal animals, or in experimental disease models. For administration to animals, antisense oligonucleotides are formulated in a pharmaceutically acceptable diluent, such as phosphate-buffered saline. Administration includes parenteral routes of administration. Calculation of antisense oligonucleotide dosage and dosing frequency depends upon factors such as route of administration and animal body weight. Following a period of treatment with antisense oligonucleotides, RNA is isolated from tissue and changes in ApoCIII nucleic acid expression are measured. Changes in ApoCIII protein levels are also measured.

Certain Indications

In certain embodiments, provided herein are methods of treating an individual comprising administering one or more pharmaceutical compositions as described herein. In certain embodiments, the individual has a cardiovascular disease or a metabolic disorder.

In certain embodiments, the cardiovascular disease is aneurysm, angina, arrhythmia, atherosclerosis, cerebrovascular disease, coronary heart disease, hypertension, dyslipidemia, hyperlipidemia, hypertriglyceridemia, hypercholesterolemia, stroke and the like. In certain embodiments, the dyslipidemia is chylomicronemia.

As shown in the examples below, compounds targeted to ApoCIII as described herein have been shown to modulate physiological markers or phenotypes of a cardiovascular disease. In certain of the experiments, the compounds increased HDL levels, and decreased LDL and triglyceride levels compared to untreated animals. In certain embodiments, the increase in HDL levels and decrease in LDL and triglyceride levels was associated with an inhibition of ApoCIII by the compounds.

In certain embodiments, physiological markers of a cardiovascular disease may be quantifiable. For example, HDL levels may be measured and quantified by, for example, standard lipid tests. For such markers, in certain embodiments, the marker may be increased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with a cardiovascular disease in a subject in need thereof. In certain embodiments, provided is a method for reducing the rate of onset of a symptom associated with a cardiovascular disease. In certain embodiments, provided is a method for reducing the severity of a symptom associated with a cardiovascular disease. In such embodiments, the methods comprise administering to an individual in need thereof a therapeutically effective amount of a compound targeted to an ApoCIII nucleic acid.

Cardiovascular diseases are characterized by numerous physical symptoms. Any symptom known to one of skill in the art to be associated with a cardiovascular disease can be prevented, treated, ameliorated or otherwise modulated as set forth above in the methods described above. In certain embodiments, the symptom may be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the symptom is angina. In certain embodiments, the symptom is chest pain. In certain embodiments, the symptom is shortness of breath. In certain embodiments, the symptom is palpitations. In certain embodiments, the symptom is weakness. In certain embodiments, the symptom is dizziness. In certain embodiments, the symptom is nausea. In certain embodiments, the symptom is sweating. In certain embodiments, the symptom is tachycardia. In certain embodiments, the symptom is bradycardia. In certain embodiments, the symptom is arrhythmia. In certain embodiments, the symptom is atrial fibrillation. In certain embodiments, the symptom is swelling in the lower extremities. In certain embodiments, the symptom is cyanosis. In certain embodiments, the symptom is fatigue. In certain embodiments, the symptom is fainting. In certain embodiments, the symptom is numbness of the face. In certain embodiments, the symptom is numbness of the limbs. In certain embodiments, the symptom is claudication or cramping of muscles. In certain embodiments, the symptom is bloating of the abdomen. In certain embodiments, the symptom is impaired short-term fever.

In certain embodiments, the metabolic disorders include, but are not limited to, hyperglycemia, prediabetes, diabetes (type I and type II), obesity, insulin resistance, metabolic syndrome and diabetic dyslipidemia.

In certain embodiments, compounds targeted to ApoCIII as described herein modulate physiological markers or phenotypes of a metabolic disorder. In certain embodiments, physiological markers of a metabolic disorder may be quantifiable. For example, glucose levels or insulin resistance can be measured and quantified by standard tests known in the art. For such markers, in certain embodiments, the marker may be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity or HDL levels can be measured and quantified by standard tests known in the art. For such markers, in certain embodiments, the marker may be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with a metabolic disorder in a subject in need thereof. In certain embodiments, provided is a method for reducing the rate of onset of a symptom associated with a metabolic disorder. In certain embodiments, provided is a method for reducing the severity of a symptom associated with a metabolic disorder. In such embodiments, the methods comprise administering to an individual in need thereof a therapeutically effective amount of a compound targeted to an ApoCIII nucleic acid.

Metabolic disorders are characterized by numerous physical symptoms. Any symptom known to one of skill in the art to be associated with a metabolic disorder can be prevented, treated, ameliorated or otherwise modulated as set forth above in the methods described above. In certain embodiments, the symptom may be any of, but not limited to, excessive urine production (polyuria), excessive thirst and increased fluid intake (polydipsia), blurred vision, unexplained weight loss and lethargy.

In certain embodiments, provided are methods of treating an individual comprising administering a therapeutically effective amount of one or more pharmaceutical compositions as described herein. In certain embodiments, the individual has a cardiovascular disease. In certain embodiments, administration of a therapeutically effective amount of an antisense compound targeted to an ApoCIII nucleic acid is accompanied by monitoring of ApoCIII levels or markers of cardiovascular disease, diabetes or other disease process associated with the expression of ApoCIII, to determine an individual's response to administration of the antisense compound. An individual's response to administration of the antisense compound is used by a physician to determine the amount and duration of therapeutic intervention.

In certain embodiments, administration of an antisense compound targeted to an ApoCIII nucleic acid results in reduction of ApoCIII expression by at least about 15, 20, 25, 30, 35, 40, 45, 50, 55, 60, 65, 70, 75, 80, 85, 90, 95 or 99%, or a range defined by any two of these values. In certain embodiments, ApoCIII expression is reduced to ≤50 mg/L, ≤60 mg/L, ≤70 mg/L, ≤80 mg/L, ≤90 mg/L, ≤100 mg/L, ≤110 mg/L, ≤120 mg/L, ≤130 mg/L, ≤140 mg/L, ≤150 mg/L, ≤160 mg/L, ≤170 mg/L, ≤180 mg/L, ≤190 mg/L or ≤200 mg/L.

In certain embodiments, administration of an antisense compound targeted to an ApoCIII nucleic acid results in increase in HDL levels by at least about 15, 20, 25, 30, 35, 40, 45, 50, 55, 60, 65, 70, 75, 80, 85, 90, 95 or 99%, or a range defined by any two of these values.

In certain embodiments, administration of an antisense compound targeted to an ApoCIII nucleic acid results in reduction of TG (postprandial or fasting) levels by at least about 15%, 20%, 25%, 30%, 35%, 40%, 45%, 50%, 55%, 60%, 65%, 70%, 75%, 80%, 85%, 90%, 95%, or 99%, or a range defined by any two of these values. In certain embodiments, TG (postprandial or fasting) is reduced to ≤100 mg/dL, ≤110 mg/dL, ≤120 mg/dL, ≤130 mg/dL, ≤140 mg/dL, ≤150 mg/dL, ≤160 mg/dL, ≤170 mg/dL, ≤180 mg/dL, ≤190 mg/dL, ≤200 mg/dL, ≤210 mg/dL, ≤220 mg/dL, ≤230 mg/dL, ≤240 mg/dL, ≤250 mg/dL, ≤260 mg/dL, ≤270 mg/dL, ≤280 mg/dL, ≤290 mg/dL, ≤300 mg/dL, ≤350 mg/dL, ≤400 mg/dL, ≤450 mg/dL, ≤500 mg/dL, ≤550 mg/dL, ≤600 mg/dL, ≤650 mg/dL, ≤700 mg/dL, ≤750 mg/dL, ≤800 mg/dL, ≤850 mg/dL, ≤900 mg/dL, ≤950 mg/dL, ≤1000 mg/dL, ≤1100 mg/dL, ≤1200 mg/dL, ≤1300 mg/dL, ≤1400 mg/dL, ≤1500 mg/dL, ≤1600 mg/dL, ≤1700 mg/dL, ≤1800 mg/dL or ≤1900 mg/dL. In certain embodiments, pharmaceutical compositions comprising an antisense compound targeted to ApoCIII are used for the preparation of a medicament for treating a patient suffering or susceptible to a cardiovascular disease.

Administration

The compounds or pharmaceutical compositions of the present invention can be administered in a number of ways depending upon whether local or systemic treatment is desired and upon the area to be treated. Administration can be oral or parenteral.

In certain embodiments, the compounds and compositions as described herein are administered parenterally. Parenteral administration includes intravenous, intra-arterial, subcutaneous, intraperitoneal or intramuscular injection or infusion.

In certain embodiments, parenteral administration is by infusion. Infusion can be chronic or continuous or short or intermittent. In certain embodiments, infused pharmaceutical agents are delivered with a pump. In certain embodiments, the infusion is intravenous.

In certain embodiments, parenteral administration is by injection. The injection can be delivered with a syringe or a pump. In certain embodiments, the injection is a bolus injection. In certain embodiments, the injection is administered directly to a tissue or organ. In certain embodiments, parenteral administration is subcutaneous.

In certain embodiments, formulations for parenteral administration can include sterile aqueous solutions which can also contain buffers, diluents and other suitable additives such as, but not limited to, penetration enhancers, carrier compounds and other pharmaceutically acceptable carriers or excipients.

In certain embodiments, formulations for oral administration of the compounds or compositions of the invention can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, oral formulations are those in which compounds of the invention are administered in conjunction with one or more penetration enhancers, surfactants and chelators.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of ApoCIII or the prevention, reduction, amelioration or slowing the progression of a disease or condition associated with ApoCIII.

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 μg to 100 mg per kg of body weight, or within a range of 0.001 mg-1000 mg dosing, and may be given once or more daily, weekly, monthly or yearly, or even once every 2 to 20 years. Following successful treatment, it may be desirable to have the patient undergo maintenance therapy to prevent the recurrence of the disease state, wherein the oligonucleotide is administered in maintenance doses, ranging from 0.01 μg to 100 mg per kg of body weight, once or more daily, to once every 20 years or ranging from 0.001 mg to 1000 mg dosing.

Certain Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compositions described herein and one or more other pharmaceutical agents are administered at the same time. In certain embodiments, one or more compositions of the invention and one or more other pharmaceutical agents are administered at different times. In certain embodiments, one or more compositions described herein and one or more other pharmaceutical agents are prepared together in a single formulation. In certain embodiments, one or more compositions described herein and one or more other pharmaceutical agents are prepared separately.

In certain embodiments, second agents include, but are not limited to, ApoCIII lowering agent, cholesterol lowering agent, non-HDL lipid lowering (e.g., LDL) agent, HDL raising agent, fish oil, niacin, fibrate, statin, DCCR (salt of diazoxide), glucose-lowering agent and/or anti-diabetic agents. In certain embodiments, the first agent is administered in combination with the maximally tolerated dose of the second agent. In certain embodiments, the first agent is administered to a subject that fails to respond to a maximally tolerated dose of the second agent.

Examples of ApoCIII lowering agents include an ApoCIII antisense oligonucleotide different from the first agent, niacin or an Apo B antisense oligonucleotide.

Examples of glucose-lowering and/or anti-diabetic agents include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

The cholesterol or lipid lowering therapy can include, but is not limited to, a therapeutic lifestyle change, statins, bile acids sequestrants, nicotinic acid and fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like.

HDL increasing agents include cholesteryl ester transfer protein (CETP) inhibiting drugs (such as Torcetrapib), peroxisome proliferation activated receptor agonists, Apo-A1, Pioglitazone and the like.

Certain Treatment Populations

Certain subjects with high TG levels are at a significant risk of cardiovascular and metabolic disease. In many subjects with high TG (e.g., hypertriglyceridemia), current treatments cannot reduce their TG levels to safe levels. ApoCIII plays an important role in TG metabolism and is an independent risk factor for cardiovascular disease. ApoCIII inhibition, as shown herein, significantly decreases TG levels which can ameliorate cardiovascular or metabolic disease, or the risk thereof.

Borderline high TG levels (150-199 mg/dL) are commonly found in the general population and are a common component of the metabolic syndrome/insulin resistance states. High plasma TG level of ≥200 mg/dL is a common clinical trait associated with an increased risk of cardiovascular disease (Hegele et al., *Hum Mol Genet* 2009, 18:4189-4194; Hegele and Pollex, *Mol Cell Biochem,* 2009, 326:35-43). Very high TG levels (≥500 and ≤2000 mg/dL) are most often associated with elevated chylomicron levels as well, and are accompanied by increasing risk for acute pancreatitis.

In certain embodiments, the compounds, compositions and methods disclosed herein are used to treat subjects with a TG level between 100-200 mg/dL, 100-300 mg/dL, 100-400 mg/dL, 100-500 mg/dL, 200-500 mg/dL, 300-500 mg/dL, 400-500 mg/dL, 500-1000 mg/dL, 600-1000 mg/dL, 700-1000 mg/dL, 800-1000 mg/dL, 900-1000 mg/dL, 500-1500 mg/dL, 1000-1500 mg/dL, 100-2000 mg/dL, 150-2000 mg/dL, 200-2000 mg/dL, 300-2000 mg/dL, 400-2000 mg/dL, 500-2000 mg/dL, 600-2000 mg/dL, 700-2000 mg/dL, 800-2000 mg/dL, 900-2000 mg/dL, 1000-2000 mg/dL, 1100-2000 mg/dL, 1200-2000 mg/dL, 1300-2000 mg/dL, 1400-2000 mg/dL, or 1500-2000 mg/dL. In certain embodiments, treatment with the compounds disclosed herein is indicated for a subject with a TG level of ≥100 mg/dL, ≥110 mg/dL, ≥120 mg/dL, ≥130 mg/dL, ≥140 mg/dL, ≥150 mg/dL, ≥160 mg/dL, ≥170 mg/dL, ≥180 mg/dL, ≥190 mg/dL, ≥200 mg/dL, ≥300 mg/dL, ≥400 mg/dL, ≥500 mg/dL, ≥600 mg/dL, ≥700 mg/dL, ≥800 mg/dL, ≥900 mg/dL, ≥1000 mg/dL, ≥1100 mg/dL, ≥1200 mg/dL, ≥1300 mg/dL, ≥1400 mg/dL, ≥1500 mg/dL, ≥1600 mg/dL, ≥1700 mg/dL, ≥1800 mg/dL, ≥1900 mg/dL, ≥2000 mg/dL, ≥2100 mg/dL, ≥2200 mg/dL, ≥2300 mg/dL, ≥2400 mg/dL or ≥2500 mg/dL.

Some types of hypertriglyceridemia can be characterized by the Fredrickson classification system or by the classification system described by Tremblay (Tremblay et al., *J Clin Lipidol,* 2011, 5:37-44). In certain embodiments, the compounds, compositions and methods described herein are useful in treating subjects with, or at risk for, Fredrickson Type II, IV or V hypertriglyceridemia.

Fredrickson Type IIb (also known as familial combined hyperlipoproteinemia) is a mixed hyperlipidemia (high cholesterol and TG levels), caused by elevations in LDL-C and in VLDL. The high VLDL levels are due to overproduction of substrates, including TG, acetyl CoA, and an increase in B-100 synthesis. They may also be caused by the decreased clearance of LDL. Prevalence in the population is about 10%.

Fredrickson Type IV (also known as familial hypertriglyceridemia) is an autosomal dominant condition occurring in approximately 1% of the population. TG levels are elevated as a result of excess hepatic production of VLDL or heterozygous LPL deficiency, but are almost always less than 1000 mg/dL. Serum cholesterol levels are usually within normal limits. The disorder is heterogeneous and the phenotype strongly influenced by environmental factors, particularly carbohydrate and ethanol consumption. In certain embodiments, the compounds, compositions and methods described herein are useful in treating subjects with a TG level ≥200 mg/dL and heterozygous LPL deficiency or VLDL overproduction. In certain embodiments, the compounds, compositions and methods described herein are useful in treating subjects with a TG level ≥500 mg/dL and heterozygous LPL deficiency or VLDL overproduction.

Fredrickson Type V has high VLDL and chylomicrons. It is characterized by carriers of loss-of-function LPL gene variants associated with LPL activity of at least 20% (i.e. partial LPL deficiency). These subjects present with lactescent plasma and severe hypertriglyceridemia because of chylomicrons and VLDL. TG levels are invariably greater than 1000 mg/dL and total cholesterol levels are always elevated. The LDL-C level is usually low. It is also associated with increased risk for acute pancreatitis, glucose intolerance and hyperuricemia. Symptoms generally present in adulthood (>35 years) and, although the prevalence is relatively rare, it is much more common than homozygous or compound heterozygous LPL deficient subjects. In certain embodiments, the compounds, compositions and methods described herein are useful in treating subjects with ≥1000 mg/dL TG. In certain embodiments, the compounds, compositions and methods described herein are useful in treating subjects with, or at risk for, pancreatitis associated with high TG levels in a subject. In certain embodiments, the compounds, compositions and methods described herein are useful in treating subjects with, or at risk for, cardiovascular or metabolic disease associated with high TG levels in a subject. In certain embodiments, the cardiovascular disease is aneurysm, angina, arrhythmia, atherosclerosis, cerebrovascular disease, coronary heart disease, hypertension, dyslipidemia, hyperlipidemia, hypertriglyceridemia, hypercholesterolemia, stroke and the like. In certain embodiments, the dyslipidemia is chylomicronemia. In certain embodiments, the metabolic diseases or disorders include, but are not limited to, hyperglycemia, prediabetes, diabetes (type I and type II), obesity, insulin resistance, metabolic syndrome and diabetic dyslipidemia.

In certain embodiments, treatment with the compounds disclosed herein is indicated for a human animal with a genetic defect that increases ApoCIII levels and/or triglyceride levels. In certain embodiments, the genetic defect is an allelic variant or polymorphism that increases ApoCIII expression. In certain embodiments, the polymorphism are T (at position 74) to A, C (at position −641) to A, G (at position −630) to A, T (at position −625) to deletion, C (at position −482) to T, T (at position −455) to C, C (at position 1100) to T, C (at position 3175) to G, T (at position 3206) to G, C (at position 3238) to G, and the like. In certain embodiments, the genetic defect is a heterozygous LPL deficiency.

In certain embodiments, treatment with the compounds disclosed herein is indicated for a human animal with elevated ApoCIII levels. In certain embodiments, the elevated ApoCIII level is ≥50 mg/L, ≥60 mg/L, ≥70 mg/L, ≥80 mg/L, ≥90 mg/L, ≥100 mg/L, ≥110 mg/L, ≥120 mg/L, ≥130 mg/L, ≥140 mg/L, ≥150 mg/L, ≥160 mg/L, ≥170 mg/L, ≥180 mg/L, ≥190 mg/L, ≥200 mg/L, ≥300 mg/L, ≥400 mg/L or ≥500 mg/L.

EXAMPLES

Non-limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Effect of in vivo Antisense Inhibition of Human ApoCIII in huApoCIII Transgenic Mice Transgenic mice with the human ApoCIII transgene utilized in the study were the progeny of huApoCIII transgenic F1 hybrids (Jackson Laboratories, CA) and C57BL/6 mice. ISIS 304801 (previously disclosed in U.S. Pat. No. 7,598,227) with a start site of 508 on SEQ ID NO: 1 (GENBANK Accession No. NM_000040.1) and a start site of 3139 on SEQ ID NO: 2 (GENBANK Accession NT_033899.8 truncated from nucleotides 20263040 to 20266203), with the sequence 5'-AGCTTCTTGTCCAGCTTTAT-3' (SEQ ID NO: 3) and a 5-10-5 MOE gapmer motif was utilized in this assay. Another ISIS antisense oligonucleotide, 'Compound X', with a 5-10-5 MOE gapmer motif, targeting another region of SEQ ID NO: 1 or SEQ ID NO: 2, was also included in this assay. Another ISIS antisense oligonucleotide, 'Compound Y', with a 5-10-5 MOE gapmer motif, targeting a rodent ApoCIII sequence (GenBank Accession No. NM_023114.3; SEQ ID NO: 5) was also included in this assay.

Treatment

Human ApoCIII transgenic mice were maintained on a 12-hour light/dark cycle and fed ad libitum Teklad lab chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

Male and female mice were assayed separately. The male mice were divided into three treatment groups consisting of 5 mice each. Two such groups received subcutaneous injections of ISIS 304801 or Compound X at a dose of 37.5 mg/kg twice a week for 2 weeks. One group of mice received subcutaneous injections of PBS twice a week for 2 weeks. The female mice were divided into four treatment groups consisting of 4-5 mice each. Three such groups received subcutaneous injections of ISIS 304801, Compounds X or Y at a dose of 37.5 mg/kg twice a week for 2 weeks. One group of mice received subcutaneous injections of PBS twice a week for 2 weeks. Prior to the treatment as well as after the last dose, blood was withdrawn from each mouse and plasma samples analyzed. Two days following the final dose, the mice were euthanized, organs harvested and analyses done.

Cholesterol and Triglyceride Levels

Plasma triglycerides and cholesterol were extracted by the method of Bligh and Dyer (Bligh, E. G. and Dyer, W. J. Can. J. Biochem. Physiol. 37: 911-917, 1959) and measured with a commercially available triglyceride kit (DCL Triglyceride Reagent; Diagnostic Chemicals Ltd.).

The results of the triglyceride analyses in males and females are presented in Tables 1 and 2, and are expressed in mg/dL. As observed, triglyceride levels in all the treatment groups were significantly lowered compared to that in the control groups.

For measuring the different fractions of cholesterol (HDL, LDL and VLDL), the plasma samples from the female groups were analyzed by HPLC and are presented in Table 3. As observed, antisense inhibition of ApoCIII significantly decreased VLDL and also significantly increased levels of HDL. An increase in HDL and a decrease in VLDL levels is a cardiovascular beneficial effect of antisense inhibition of ApoCIII and can be beneficial to animals with, or at risk or, dyslipidemic diseases.

TABLE 1

Effect of antisense oligonucleotide treatment on triglyceride levels (mg/dL) in female transgenic mice

|  | Week 0 | Week 2 | % change |
|---|---|---|---|
| PBS | 2144 | 2533 | +21 |
| Compound X | 2385 | 677 | −72 |
| Compound Y | 2632 | 1644 | −37 |
| ISIS 304801 | 2390 | 542 | −75 |

TABLE 2

Effect of antisense oligonucleotide treatment on triglyceride levels (mg/dL) in male transgenic mice

|  | Week 0 | Week 2 | % Change |
|---|---|---|---|
| PBS | 6191 | 7073 | +14 |
| ISIS 304801 | 6588 | 780 | −88 |
| Compound X | 5464 | 861 | −84 |

TABLE 3

Effect of antisense oligonucleotide treatment on plasma cholesterol fractions (% total cholesterol) in female transgenic mice

|  | VLDL (%) | LDL (%) | HDL (%) |
|---|---|---|---|
| PBS | 77 ± 2.6 | 4 ± 1.0 | 19 ± 1.9 |
| ISIS 304801 | 41 ± 0.6 | 7 ± 0.3 | 52 ± 0.5 |
| Compound X | 46 ± 5.1 | 7 ± 1.0 | 48 ± 5.8 |

Example 2

Dose-dependent Antisense Inhibition of Human ApoCIII in huApoCIII Transgenic Mice ISIS 304801 and Compound X were further studied in a dose-dependent study using human ApoCIII transgenic mice.
Treatment Human ApoCIII transgenic mice were maintained on a 12-hour light/dark cycle and fed ad libitum Teklad lab chow. Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

Female mice were divided into nine treatment groups consisting of 3 mice each. Eight such groups received subcutaneous injections of ISIS 304801 or compound X at a dose of 1.5 mg/kg/week, 5 mg/kg/week, 15 mg/kg/week, or 50 mg/kg/week for 2 weeks. One group of mice received subcutaneous injections of PBS for 2 weeks. Prior to the treatment as well as after the last dose, blood was withdrawn from each mouse and plasma samples analyzed. Two days following the final dose, the mice were euthanized, organs harvested and analyses done.
Cholesterol and Triglyceride Levels Plasma triglycerides and cholesterol were extracted by the method of Bligh and Dyer (Bligh, E. G. and Dyer, W. J. Can. J. Biochem. Physiol. 37: 911-917, 1959) and measured with a commercially available triglyceride kit (DCL Triglyceride Reagent, Diagnostic Chemicals Ltd.).

The results of the cholesterol and triglyceride analyses in the mice are presented in Tables 4 and 5, and are expressed in mg/dL. As observed, HDL levels in mice treated with higher doses of ISIS 304801 were significantly elevated, indicating the beneficial effect of inhibition of ApoCIII by the oligonucleotides. LDL and triglyceride levels in the high dose treatment groups were lowered compared to that in the control groups. An increase in HDL and a decrease in LDL and TG levels is a cardiovascular beneficial effect of antisense inhibition of ApoCIII and can be beneficial to animals with, or at risk of, dyslipidemic diseases.

TABLE 4

Effect of antisense oligonucleotide treatment on cholesterol and triglyceride levels (mg/dL) in transgenic mice

|  | Dose (mg/kg/wk) | Total Cholesterol | Triglycerides |
|---|---|---|---|
| PBS | — | 124 | 1017 |
| ISIS 304801 | 50.0 | 105 | 417 |
|  | 15.0 | 116 | 593 |
|  | 5.0 | 101 | 871 |
|  | 1.5 | 125 | 1092 |
| Compound X | 50.0 | 90 | 496 |
|  | 15.0 | 127 | 1168 |
|  | 5.0 | 166 | 1506 |
|  | 1.5 | 168 | 1518 |

TABLE 5

Effect of antisense oligonucleotide treatment on HDL and LDL cholesterol levels (mg/dL) in transgenic mice

|  | Dose (mg/kg/wk) | HDL | LDL |
|---|---|---|---|
| PBS | — | 40 ± 8 | 42 ± 8 |
| ISIS 304801 | 50.0 | 62 ± 19 | 28 ± 7 |
|  | 15.0 | 60 ± 9 | 34 ± 7 |
|  | 5.0 | 44 ± 3 | 30 ± 13 |
|  | 1.5 | 39 ± 2 | 40 ± 2 |
| Compound X | 50.0 | 46 ± 10 | 25 ± 3 |
|  | 15.0 | 37 ± 7 | 40 ± 2 |
|  | 5.0 | 40 ± 10 | 47 ± 5 |
|  | 1.5 | 45 ± 7 | 44 ± 6 |

Example 3

Effect of Antisense Inhibition of ApoCIII in CETP Transgenic LDL Receptor Null Mice Compound Y was further studied in a human CETP transgenic LDLr$^{-/-}$ mouse model to examine the effects of a mouse ApoCIII antisense inhibitor on plasma lipids and lipoprotein metabolism in hyperlipidemic mice.
Treatment Human CETP transgenic LDLr$^{-/-}$ transgenic mice were maintained on a 12-hour light/dark cycle and fed ad libitum a western diet (42% calories from fat, 0.2% cholesterol). Animals were acclimated to this diet for 10 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

Eight week old male mice were divided into three treatment groups. One such group of 6 mice received subcutaneous injections of compound Y at a dose of 12.5 mg/kg/week for 4 weeks. One group of 4 mice received subcutaneous injections of the control oligonucleotide ISIS 141923 (SEQ ID NO: 4) at a dose of 12.5 mg/kg/week for 4 weeks. One group of 5 mice received subcutaneous injections of PBS for 4 weeks. Plasma samples were taken at prior to the start of dosing, and at 2 and 4 weeks of treatment.

Cholesterol and Triglyceride Levels

Plasma triglycerides and cholesterol were extracted by the method of Bligh and Dyer (Bligh, E. G. and Dyer, W. J. Can. J. Biochem. Physiol. 37: 911-917, 1959) and measured with a commercially available triglyceride kit (DCL Triglyceride Reagent; Diagnostic Chemicals Ltd.).

The results of the cholesterol and triglyceride analyses in the mice are presented in Tables 6 to 7, and are expressed in mg/dL. Cholesterol and triglyceride levels in the treatment group were significantly lowered compared to those in the control group. A decrease in cholesterol and TG levels is a cardiovascular beneficial effect of antisense inhibition of ApoCIII and can be beneficial to animals with, or at risk of, dyslipidemic diseases.

TABLE 6

Effect of antisense oligonuceotide treatment on cholesterol levels (mg/dL) in transgenic mice

| Week | PBS | Compound Y |
|---|---|---|
| 0 | 1851 | 1747 |
| 2 | 2035 | 878 |
| 4 | 2359 | 686 |

TABLE 7

Effect of antisense oligonucleotide treatment on triglyceride levels (mg/dL) in transgenic mice

| Week | PBS | Compound Y |
|---|---|---|
| 0 | 297 | 451 |
| 2 | 420 | 150 |
| 4 | 496 | 86 |

Inhibition of CETP Protein Levels and Activity

Plasma CETP protein levels were measured using a commercial ELISA kit (ALPCO, Cat#47-CETHU-E01). CETP protein activity was measured using a fluorometric assay kit (Roar Biomedical, Inc. Cat# RB-CETP). As presented in Table 8, treatment with antisense oligonucleotide reduced CETP protein expression and activity. CETP (cholesteryl ester transfer protein) facilitates the exchange of triglycerides and cholesterol esters between high density lipoproteins (HDL) and apoB-containing lipoproteins, such as very low density lipoproteins (VLDL), LDL and chylomicrons. A decrease in CETP is associated with increased HDL levels and decreased LDL levels (Barter P. J. et al. Artherioscler. Thromb. Vasc. Biol. 23: 160-167, 2003). Therefore, inhibition of CETP protein levels and activity is a cardiovascular beneficial effect of antisense inhibition of ApoCIII and can be beneficial to animals with, or at risk of, dyslipidemic diseases. The control oligonucleotide did not have any significant effect on CETP, as expected.

TABLE 8

Percent inhibition of CETP protein in transgenic mice

| | Level | Activity |
|---|---|---|
| Compound Y | 24 | 24 |
| ISIS 141923 | 0 | 3 |

Increase of apoA1 Protein Levels and Paraoxanase-1 (PON1) Activity

Plasma ApoA1 protein levels were measured by ELISA. PON1 protein activity was measured using a EnzChek® Paroxanase fluorometric assay kit (Invitrogen, Cat# E33702). As presented in Tables 9 and 10, treatment with antisense oligonucleotide enhanced ApoA1 protein expression and increased PON1 protein activity. ApoA1 and PON1 are major protein components of HDL in plasma (Aviram, M and Rosenblat, M. Curr. Opin. Lipidol. 16: 393-399, 2005). Therefore, enhancement of protein level and activity of these two protein components is a cardiovascular beneficial effect of antisense inhibition of ApoCIII and can be beneficial to animals with, or at risk of, dyslipidemic diseases. The control oligonucleotide did not have any effect on either protein, as expected.

TABLE 9

Percent increase in APOA1 protein levels in transgenic mice

| | mg/dL |
|---|---|
| PBS | 65 |
| Compound Y | 211 |
| ISIS 141923 | 106 |

TABLE 10

Percent increase in PON1 protein activity in transgenic mice

| Minutes | PBS | Compound Y | ISIS 141923 |
|---|---|---|---|
| 15 | 0.2 | 0.5 | 0.2 |
| 30 | 0.8 | 1.1 | 0.8 |
| 60 | 2.3 | 3.5 | 2.3 |
| 120 | 4.9 | 7.5 | 4.8 |
| 180 | 7.7 | 11.6 | 7.6 |

Example 4

Effect of Antisense Inhibition of ApoCIII on HDL Cholesterol Clearance in CETP Transgenic LDL Receptor Null Mice Compound Y was further studied in a human CETP transgenic LDLr$^{-/-}$ mouse model to examine the effects of an ApoCIII antisense inhibitor on HDL cholesterol clearance and metabolism in hyperlipidemic mice.

Treatment

Human CETP transgenic LDLr$^{-/-}$ mice were maintained on a 12-hour light/dark cycle and fed ad libitum a western diet (42% calories from fat, 0.2% cholesterol). Animals were acclimated to this diet for 10 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

Eight week old male mice were divided into three treatment groups. One group of 6 mice received subcutaneous injections of compound Y at a dose of 15 mg/kg/week for 6 weeks. One group of 4 mice received subcutaneous injections of the control oligonucleotide ISIS 141923 at a dose of 15 mg/kg/week for 6 weeks. One group of 5 mice received subcutaneous injections of PBS for 6 weeks.

Cholesterol and Triglyceride Levels

Plasma triglycerides and cholesterol were extracted by the method of Bligh and Dyer (Bligh, E. G. and Dyer, W. J. Can. J. Biochem. Physiol. 37: 911-917, 1959) and measured with a commercially available triglyceride kit (DCL Triglyceride Reagent; Diagnostic Chemicals Ltd.).

The results of the cholesterol and triglyceride analyses in the mice are presented in Table 11, and are expressed in mg/dL. Cholesterol and triglyceride levels in the treatment group was significantly lowered compared to that in the control group. A decrease in cholesterol and TG levels is a cardiovascular beneficial effect of antisense inhibition of ApoCIII and can be beneficial to animals with, or at risk of, dyslipidemic diseases.

TABLE 11

Effect of antisense oligonucleotide treatment on cholesterol and triglyceide levels (mg/dL) in transgenic mice

|  | Total cholesterol | Triglycerides |
| --- | --- | --- |
| PBS | 2188 | 641 |
| Compound Y | 1402 | 170 |

HDL Clearance

Mice from all groups were injected via tail vein with 1×10$^6$ dpm of $^3$H-cholesteryl ether ($^3$H-CEth)-labeled HDL. The radiolabeled cholesteryl ether is structurally similar to cholesterol but it will be trapped in tissues that take it up. Therefore, the clearance of the radiolabeled cholesteryl ether from plasma and it's accumulation in the liver can be used to evaluate effects on reverse cholesterol transport. Plasma samples were collected at 5 min, 1.5 hrs, 3 hrs, 6 hrs and 24 hrs post-injection and the radioactivity was counted using a liquid scintillation counter. At 24 hours, the mice were sacrificed and liver were harvested. The liver samples were extracted in 2:1 Chloroform/Methanol and the extract was blown down under nitrogen gas, solubilized in scintillation cocktail and counted using the same liquid scintillation counter.

The decrease in radiolabel, as presented in Table 12 is associated with the clearance of HDL-Ceth from the plasma. The results indicate that treatment with Compound Y lead to enhanced rate of HDL cholesterol clearance from the plasma. This was associated with the greater accumulation of radiolabeled cholesteryl etherin the liver of Compound Y-treated mice, as presented in Table 13. Therefore, the data indicates that inhibition of ApoCIII in these transgenic mice improves reverse cholesterol transport and, therefore, would have a beneficial effect on patients with cardiovascular disease such as patients with a dyslipidemic disease.

TABLE 12

Effect of antisense oligonucleotide treatment on plasma HDL cholesterol (% of count at 0 hrs) in transgenic mice

|  | 1.5 hr | 3 hr | 6 hr | 24 hr |
| --- | --- | --- | --- | --- |
| PBS | 87 | 79 | 64 | 38 |
| ISIS 141923 | 84 | 82 | 69 | 39 |
| Compound Y | 78 | 71 | 57 | 25 |

TABLE 13

Effect of antisense oligonucleotide treatment on hepatic uptake of radiolabeled CEth in transgenic mice

|  | % Increase (dpm/g liver tissue) |
| --- | --- |
| ISIS 141923 | 0 |
| Compound Y | 14 |

Example 5

Comparison of the Effect of Antisense Inhibition of Human ApoCIII in C57BL/6 Mice with an ApoCIII Knockout Mouse Model ApoCIII knockout mice were obtained from Jackson Laboratories (stock number 002057) and were compared to ApoCIII antisense oligonucleotide treated C57BL/6 mice. Compound Z, with a 5-10-5 MOE gapmer motif and targeting a rodent ApoCIII sequence (GenBank Accession No. NM_023114.3; SEQ ID NO: 5) was used in this study.

Antisense Oligonucleotide Treatment

C57BL/6 mice were maintained on a 12-hour light/dark cycle and fed a high fat diet (Harland Teklad lab chow #88137) for one week. Antisense oligonucleotides (ASOs) were prepared in PBS and sterilized by filtering through a 0.2 micron filter. Oligonucleotides were dissolved in 0.9% PBS for injection. The mice were randomized based on total plasma cholesterol and triglyceride levels into groups of 6-8 mice each. Three groups of C57BL/6 mice received weekly intraperitoneal injections of Compound Z at doses of 3.1 mg/kg, 6.3 mg/kg, or 12.5 mg/kg for a period of 6 weeks. A group of C57BL/6 mice received weekly intraperitoneal injections of PBS for a period of 6 weeks. The PBS group served as a control to which the oligonucleotide-treated groups and the ApoCIII knockout mice were compared.

Two days after the final dose, the mice were sacrificed and organs harvested. Similar groups of mice fed a normal murine chow were also tested.

Liver Triglycerides

Liver triglycerides were with an Olympus clinical analyzer (Hitachi Olympus AU400e, Melville, N.Y.). The data is presented in Table 14 and demonstrates that mice treated with an ApoCIII antisense oligonucleotide have a different phenotype than ApoCIII knockout mice. The high dose ApoCIII antisense oligonucleotide treated mice had liver triglyceride levels similar to that of the PBS control. Liver triglyceride levels in the ApoCIII knockout mice were significantly higher than in C57BL/6 mice treated with an ApoCIII antisense oligonucleotide or the PBS control. Therefore, antisense inhibition of ApoCIII had the beneficial effect of lowering the risk of liver steatosis compared to the ApoCIII knockout mouse model.

TABLE 14

Liver triglyceride levels (mg/g liver tissue)

|  | Dose (mg/kg) | High-fat diet fed |
|---|---|---|
| PBS | — | 33 |
| Compound Z | 3.1 | 44 |
|  | 6.3 | 47 |
|  | 12.5 | 33 |
| ApoCIII KO | — | 60 |

Example 6

Effect of in vivo Antisense Inhibition of ApoCIII in C57BL/6 Mice

The effect of antisense inhibition of ApoCIII on plasma lipid levels and fat clearance was evaluated.

Treatment

Male C57/BL6 mice were maintained on a 12-hour light/dark cycle and fed ad libitum a western diet (Harland Tekland 88137). Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

Groups of 7-8 mice each received intraperitoneal injections of Compound Z at a dose of 12.5 mg/kg/wk for 6 weeks. Another group of mice received intraperitoneal injections of control oligonucleotide ISIS 141923 at a dose of 12.5 mg/kg/wk for 6 weeks. A third group of mice received intraperitoneal injections of PBS for 6 weeks. Two days after the final dose, the mice were fasted for 4 hours, sacrificed and plasma and tissues were collected.

Inhibition of ApoCIII mRNA

Total RNA was extracted from the liver and small intestine and ApoCIII mRNA was quantitated by RT-PCR using an ApoCIII primer probe set and normalized to cyclophilin. The results are presented in Table 15, expressed as percent inhibition of ApoCIII mRNA compared to the PBS control. ISIS 141923 did not cause any reduction in ApoCIII mRNA levels, as expected. The data demonstrated the significant inhibition of ApoCIII mRNA in the liver and small intestine by Compound Z compared to the PBS control.

Inhibition of intestinal ApoCIII expression could be important in the prevention of chylomicronemia (Chait et al., 1992, *Adv Intern Med.* 1992, 37:249-73), a dyslipidemic state caused by improper clearance of chylomicron triglyceride. Severe forms of chylomicronemia can lead to pancreatitis, a life-threatening condition. By inhibiting intestinal ApoCIII, inhibition of lipoprotein lipase would be reduced, and chylomicron triglyceride clearance would be enhanced, thereby preventing pancreatitis. In addition, inhibition of intestinal ApoCIII would enhance clearance of postprandial triglyceride, thereby lowering post prandial TG a known risk factor for coronary heart disease.

TABLE 15

Percent inhibition of ApoCIII mRNA relative to the PBS control

|  | % inhibition |
|---|---|
| Liver | 74 |
| Small Intestine | 13 |

Cholesterol and Triglyceride Levels

Plasma cholesterol were extracted by the method of Bligh and Dyer (Bligh, E. G. and Dyer, W. J. Can. J. Biochem. Physiol. 37: 911-917, 1959) and measured with an Olympus clinical analyzer (Hitachi Olympus AU400e, Melville, N.Y.). HDL and non-HDL cholesterol were individually measured by HPLC. Triglyceride levels were measured with the use of a commercially available triglyceride kit (DCL Triglyceride Reagent; Diagnostic Chemicals Ltd., Charlottetown, Canada). The results are presented in Table 16 and are expressed in mg/dL. Treatment with Compound Z resulted in significant reduction of total cholesterol, non-HDL cholesterol and plasma triglyceride levels compared to the PBS control. A decrease in total cholesterol, non-HDL cholesterol and TG levels is a cardiovascular beneficial effect of antisense inhibition of ApoCIII and can be beneficial to animals with, or at risk of, dyslipidemic diseases.

TABLE 16

Plasma cholesterol and triglyceride levels (mg/dL) in C56BL/6 mice

| Treatment | Dose (mg/kg/wk) | Total cholesterol | HDL cholesterol | LDL cholesterol | VLDL cholesterol | Triglycerides |
|---|---|---|---|---|---|---|
| PBS | — | 93 | 70 | 20 | 2.9 | 84 |
| ISIS 141923 | 12.5 | 97 | 78 | 19 | 2.1 | 82 |
| Compound Z | 12.5 | 95 | 75 | 17 | 3.1 | 70 |

Fat Clearance

Plasma samples were collected at 30 min, 1 hr, 2 hrs, 3 hrs, and 4 hrs post-injection and plasma total lipid content was measured with an Olympus clinical analyzer (Hitachi Olympus AU400e, Melville, N.Y.). The lipid level in the plasma, as presented in Table 17 was an inverse indicator of lipid clearance from the plasma. The results indicate that treatment with Compound Z lead to enhanced rate of fat clearance from the plasma.

Therefore, the data indicates that inhibition of ApoCIII in these transgenic mice improves reverse cholesterol transport and, would have a beneficial effect on patients with cardiovascular disease.

TABLE 17

Effect of antisense oligonucleotide treatment on plasma lipid (mg/dL) in C57BL/6 mice

| | 0 hr | 0.5 hr | 1 hr | 2 hr | 3 hr | 4 hr | Area under the curve |
|---|---|---|---|---|---|---|---|
| PBS | 86 | 80 | 64 | 122 | 118 | 90 | 23631 |
| ISIS 141923 | 115 | 142 | 124 | 236 | 225 | 150 | 43677 |
| Compound Z | 66 | 55 | 96 | 156 | 151 | 101 | 28371 |

Example 7

Effect of in vivo Antisense Inhibition of ApoCIII in C57BL/6 Mice

The effect of antisense inhibition of ApoCIII on ApoCIII expression levels and fat clearance was evaluated.

Treatment

Male C57/BL6 mice were maintained on a 12-hour light/dark cycle and fed ad libitum a western diet (Harland Tekland 88137). Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

Groups of 5 mice each received intraperitoneal injections of an ApoCIII targeting antisense oligonucleotide, Compound Z, at a dose of 12.5 mg/kg/wk for 6 weeks. Another group of mice received intraperitoneal injections of control oligonucleotide ISIS 141923 at a dose of 12.5 mg/kg/wk for 6 weeks. Two days after the final dose, the mice were fasted overnight, and a bolus of 200 µL of olive oil was administered by oral gavage. Following the bolus, plasma triglyceride levels were measured at regular intervals for 4 hours. The mice were sacrificed and plasma and tissues were collected.

Inhibition of ApoCIII mRNA

Total RNA was extracted from the liver and small intestine and ApoCIII mRNA was quantitated by RT-PCR using an ApoCIII primer probe set and normalized to cyclophilin. The results are presented in Table 18, expressed as percent inhibition of ApoCIII mRNA compared to the oligonucleotide control. The data demonstrated the significant inhibition of ApoCIII mRNA in the liver and small intestine by Compound Z compared to the olionucleotide control.

As noted elsewhere herein, inhibition of intestinal ApoCIII expression could be important in the prevention of chylomicronemia (Chait et al., 1992, Adv Intern Med. 1992, 37:249-73), a dyslipidemic state caused by improper clearance of chylomicron triglyceride. Severe forms of chylomicronemia can lead to pancreatitis, a life-threatening condition. By inhibiting intestinal ApoCIII, inhibition of lipoprotein lipase would be reduced, and chylomicron triglyceride clearance would be enhanced, thereby preventing pancreatitis. In addition, inhibition of intestinal ApoCIII would enhance clearance of postprandial triglyceride, thereby lowering post prandial TG a known risk factor for coronary heart disease.

TABLE 18

Percent inhibition of ApoCIII mRNA relative to the control oligonucleotide treated C57/BL/6 mice

| Strain of mice | | % inhibition |
|---|---|---|
| C57BL/6 | Liver | 74 |
| | Small Intestine | 60 |

Fat Clearance

Plasma samples were collected at 0 min, 30 min, 60 min, 120 min, 180 min, and 240 min post-injection and plasma triglyceride concentrations was measured with an Olympus clinical analyzer (Hitachi Olympus AU400e, Melville, N.Y.). The results indicate that treatment with Compound Z lead to enhanced rate of triglyceride clearance from the plasma.

This study can be compared to fat bolus clinical studies in which patients expressing high apo-CIII levels showed increased postprandial TG concentrations (Petersen K. F. et al., N Engl J Med 2010; 362: 1082-1089).

TABLE 19

Effect of antisense oligonucleotide treatment on postprandial plasma TG (mg/dL) in C57BL/6 mice

| Strain of mice | | 0 min | 30 min | 60 min | 120 min | 180 min | 240 min |
|---|---|---|---|---|---|---|---|
| C57BL/6 | ISIS 141923 | 115 | 142 | 124 | 236 | 225 | 150 |
| | Compound Z | 66 | 55 | 96 | 156 | 151 | 101 |

Example 8

Effect of in vivo Antisense Inhibition of ApoCIII in C57BL/6 Mice

The effect of antisense inhibition of ApoCIII on fat clearance was evaluated.

Treatment

Male C57/BL6 mice were maintained on a 12-hour light/dark cycle and fed ad libitum a western diet (Harland Tekland 88137). Animals were acclimated for at least 7 days in the research facility before initiation of the experiment. Antisense oligonucleotides (ASOs) were prepared in PBS and sterilized by filtering through a 0.2 micron filter. Oligonucleotides were dissolved in 0.9% PBS for injection.

Groups of 6 mice each received intraperitoneal injections of an ApoCIII targeting antisense oligonucleotide, Compound Y or Compound Z, at a dose of 12.5 mg/kg/wk, 6.3 mg/kg/week or 3.1 mg/kg/week for 6 weeks. Another group of mice received intraperitoneal injections of control oligonucleotide ISIS 141923 at a dose of 12.5 mg/kg/wk for 6 weeks. Another group of mice received intraperitoneal injections of PBS for 6 weeks. Two days after the final dose, the mice were fasted overnight, and a bolus of 200 µL of olive oil was administered by oral gavage. Following the bolus, plasma triglyceride levels were measured at regular intervals for 4 hours.

Fat Clearance

Plasma samples were collected at 0 min, 30 min, 60 min, 120 min, 180 min, and 240 min post-injection and plasma triglyceride concentrations were measured with an Olympus clinical analyzer (Hitachi Olympus AU400e, Melville, N.Y.). The results indicate that treatment with Compound Y and Compound Z lead to enhanced rate of fat clearance from the plasma. N.d. indicates that the data set was not calculated.

This study can be compared to fat bolus clinical studies in which patients expressing high apo-CIII levels showed increased postprandial TG concentrations (Petersen K. F. et al., N Engl J Med 2010; 362: 1082-1089)

TABLE 20

Effect of antisense oligonucleotide treatment on
postprandial plasma TG (mg/dL) in C57BL/6 mice

|  | Dose (mg/kg/wk) | 0 min | 30 min | 60 min | 120 min | 180 min | 240 min |
|---|---|---|---|---|---|---|---|
| PBS | — | 79 | 104 | 118 | 126 | 113 | 116 |
| ISIS 141923 | 12.5 | 75 | 100 | 116 | 150 | 138 | 133 |
| Compound Y | 12.5 | 79 | 74 | 103 | 117 | 120 | 96 |
|  | 6.3 | 64 | 70 | 81 | 94 | 120 | 112 |
|  | 3.1 | 91 | 85 | 106 | 139 | 164 | 133 |
| Compound Z | 12.5 | 73 | 65 | 84 | 118 | 94 | 76 |
|  | 6.3 | 70 | 73 | 89 | 117 | 120 | 89 |
|  | 3.1 | 86 | 98 | 143 | 137 | 152 | 128 |

Example 9

Effect of ISIS Antisense Oligonucleotides Targeting Human ApoCIII in Monkey Model of Hypertriglyceridemia Rhesus monkeys maintained on a high fructose diet were treated with ISIS 304801. Antisense oligonucleotide efficacy and tolerability, as well as the pharmacological effect were evaluated.

Treatment

The monkeys were 2-4 years old and weighed between 2 and 5 kg. The monkeys were assigned to six groups of five randomly assigned male rhesus monkeys each. About 60g of diet (Certified Primate Diet #5048, PMI Nutrition International, Inc.) was provided to each monkey in Groups 1-4 twice daily. An appropriate fructose supplement (i.e. approximately 15% Kool Aid® mixture) was supplied in the morning for 16 weeks prior to antisense oligonucleotide dosing. To confirm sufficient triglyceride level elevations, blood samples for serum chemistry were collected from all animals 1-2 weeks prior to dosing.

The groups of monkeys were injected subcutaneously with ISIS oligonucleotide or PBS using a stainless steel dosing needle and syringe of appropriate size into one of 4 sites on the back of the monkeys; each site being used per dose in a clock-wise manner. Some of the groups were dosed three times a week for the first week (Days 1, 3, and 5) as loading doses, and subsequently twice a week for weeks 2-12, with 5 mg/kg, 10 mg/kg, or 20 mg/kg of ISIS 304801. Two control groups of 5 rhesus monkeys each were injected with PBS subcutaneously three times a week for the first week (Days 1, 3, and 5), and subsequently twice a week for weeks 2-12. The dosing chart is shown in Table 21. Monkeys of Groups 1-4 were sacrificed on Day 86.

An additional high fat challenge was administered to monkeys of Groups 5 and 6 in the form of a whipping cream milk shake. The milk shake was standardized to consist of 782 calories per $m^2$ of body surface with 77.6% of calories from fat, 19.2% from carbohydrate, and 3.1% from protein. Monkeys of Groups 5 and 6 were fasted overnight and the milk shake was administered once on day 84 via a gastric tube. Blood was drawn just prior to (time=0 hours) and 1, 2, 3, 4, and 6 hours after ingestion of the fat load to assess the triglyceride excursion. The monkeys were rested and remained otherwise fasting during the 6 hours post-fat challenge. Monkeys of this group were sacrificed on Day 87.

TABLE 21

Groups of rhesus monkeys on a high fructose diet

| Group | Test Article | Weekly Dose (mg/kg/week) | Sex | No. of Animals |
|---|---|---|---|---|
| Toxicology groups | | | | |
| 1 | PBS | 0 | Male | 5 |
| 2 | ISIS 304801 | 10 | Male | 5 |
| 3 | ISIS 304801 | 20 | Male | 5 |
| 4 | ISIS 304801 | 40 | Male | 5 |
| High Fat Challenge Test groups | | | | |
| 5 | PBS | 0 | Male | 5 |
| 6 | ISIS 304801 | 40 | Male | 5 |

Hepatic Target Reduction

RNA Analysis

Approximately 150 mg of liver was collected from Groups 1-4 for ApoCIII mRNA analysis at sacrifice. The liver was divided into 2 pieces and soaked in two tubes containing RLT buffer with 1% beta-mercaptoethanol. The tissues were homogenized and ApoCIII expression was quantified by RT-PCR analysis. As shown in Table 22, treatment with ISIS 304801 resulted in significant reduction of ApoCIII mRNA in comparison to the PBS control. The

TABLE 22

Percent Inhibition of ApoCIII mRNA
in the rhesus monkey liver relative to the PBS control

| Groups | Dose (mg/kg/week) | % inhibition |
|---|---|---|
| 2 | 10 | 68 |
| 3 | 20 | 78 |
| 4 | 40 | 83 |

Protein Analysis

Approximately 1.5 mL of blood was collected from all study animals in Groups 1-4 and placed in tubes containing $K_2$-EDTA and then centrifuged for plasma separation. ApoCIII protein levels were quantified on a clinical analyzer using a commercially available turbidometric assay (Kamiya Biomedical Co., Seattle, Wash.). As shown in Table 23, treatment with ISIS 304801 resulted in significant reduction of ApoCIII protein levels in comparison to the PBS control. The kinetics of ApoCIII protein level reduction was also analyzed and is presented in Table 24.

TABLE 23

Percent Inhibition of ApoCIII plasma protein levels
in the rhesus monkey relative to the PBS control

| Groups | Dose (mg/kg/week) | % inhibition |
|---|---|---|
| 2 | 10 | 74 |
| 3 | 20 | 72 |
| 4 | 40 | 89 |

TABLE 24

ApoCIII plasma protein levels (mg/dL) on different days
in the rhesus monkey relative to the PBS control

| Groups | Dose (mg/kg/wk) | Day −7 | Day 16 | Day 30 | Day 86 |
|---|---|---|---|---|---|
| 1 | — | 4.0 | 5.5 | 3.8 | 5.7 |
| 2 | 10 | 4.8 | 3.2 | 0.2 | 1.5 |
| 3 | 20 | 4.5 | 3.8 | 0.9 | 1.6 |
| 4 | 40 | 5.2 | 2.9 | 0.0 | 0.6 |

Lipoprotein Particle Analysis

To establish the kinetics of plasma ApoCIII suppression, plasma samples were collected 7 days before the commencement of dosing, as well as on days 16, 30 and 86 of the dosing period. The samples were subjected to NMR lipoprotein particle analysis (Liposcience, Raleigh, N.C.). Since there were no significant differences in ApoCIII lowering between the treatment groups (Groups 2-4), the analyses is presented only of Group 2 (treatment group receiving 10 mg/kg/week). The data is presented in Tables 25 and 26.

Statistically significant mean changes from the baseline were observed in total plasma triglycerides (TG) and in VLDL and chylomicron TG of the treatment group at day 30. At the same time, the control monkeys demonstrated mean increases in the same parameters. Sustained treatment with ISIS 304801 in these fructose-fed monkeys led to time-dependent increases in HDL cholesterol particle numbers by approximately 8 μmol/L (Tables 27) and did not produce elevations in LDL cholesterol in these studies (Table 28). There were no significant changes in LDL cholesterol particle quantity over the 12 week treatment period, relative to the PBS control group.

At the time of sacrifice, livers were extracted using the Bligh and Dyer extraction method (Bligh E G and Dyer W J. Can J Biochem Physiol 1959; 37: 911-917) and quantified using a Wako colorimentric TG assay. Antisense inhibition of ApoCIII did not increase hepatic TG accumulation in any of the treatment groups relative to the PBS control group (Table 29).

TABLE 25

Change from baseline plasma TGmg/dL)
on different days in the rhesus monkey

| | Dose (mg/kg/wk) | Day −7 | Day 16 | Day 30 | Day 86 |
|---|---|---|---|---|---|
| PBS | — | 0 | 18 | 23 | 27 |
| ISIS 304801 | 10 | 0 | −22 | −32 | −27 |

TABLE 26

Change from baseline VLDL and chylomicron TG (mg/dL)
on different days in the rhesus monkey

| | Dose (mg/kg/wk) | Day −7 | Day 16 | Day 30 | Day 86 |
|---|---|---|---|---|---|
| PBS | — | 0 | 17 | 22 | 28 |
| ISIS 304801 | 10 | 0 | −22 | −31 | −26 |

TABLE 27

Change from baseline HDL cholesterol particles (μmol/L)
on different days in the rhesus monkey

| | Dose (mg/kg/wk) | Day −7 | Day 16 | Day 30 | Day 86 |
|---|---|---|---|---|---|
| PBS | — | 0.3 | −5.6 | −3.5 | −8.1 |
| ISIS 304801 | 10 | 0.0 | 0.5 | 9.7 | 8.0 |

TABLE 28

Total LDL cholesterol particles (nmol/L)
on different days in the rhesus monkey

| | Dose (mg/kg/wk) | Day −7 | Day 16 | Day 30 | Day 86 |
|---|---|---|---|---|---|
| PBS | — | 982 | 928 | 1005 | 1184 |
| ISIS 304801 | 10 | 1007 | 938 | 781 | 910 |

TABLE 29

Hepatic triglyceride content in PBS control and ISIS 304801 cohorts
after 12 weeks in HTG rhesus monkeys

| Liver TG (ug/mg) | Average |
|---|---|
| PBS | 9 |
| 10 mg/kg/wk | 16 |
| 20 mg/kg/wk | 18 |
| 40 mg/kg/wk | 6 |

Post-prandial Plasma TG Clearance

At 10 weeks, the post-prandial plasma TG levels in monkeys from the 10 mg/kg/week group (Group 2) were measured at 0 hr, 1 hr, 2 hr, 3 hr, and 4 hr after providing a meal to the monkeys. As shown in Tables 30 and 31, post-prandial plasma TG clearance was significantly increased, as shown by the 38% decrease in post-prandial TG area under the curve (AUC) in monkeys of the 10 mg/kg/week group.

Post-prandial TG clearance was also assessed in Groups 5 and 6 (the PBS control and 40 mg/kg/week group after a fat challenge) at 12 weeks. The data is presented in Table 32, and also indicates a significant decrease in post-prandial TG area under the curve (AUC) in monkeys of that group compared to the control.

TABLE 30

Plasma TG (mg/dL) in the rhesus monkey

| | Dose (mg/kg/wk) | 0 hr | 1 hr | 2 hr | 3 hr | 4 hr |
|---|---|---|---|---|---|---|
| PBS | — | 167 | 169 | 146 | 147 | 131 |
| ISIS 304801 | 10 | 105 | 87 | 95 | 102 | 80 |

TABLE 31

Post-prandial TG area under the curve (AUC) in the rhesus monkey

|  | AUC |
|---|---|
| PBS | 610 |
| ISIS 304801 | 376 |

TABLE 32

Post-prandial TG area under the curve (AUC) in the rhesus monkey after fat challenge

|  | AUC |
|---|---|
| PBS | 613 |
| ISIS 304801 | 405 |

Monkeys in the 10 mg/kg/wk group had lower fasting plasma TG levels than the PBS group at 10 weeks. Results in non-human primates demonstrate that antisense inhibition of ApoCIII represent an attractive therapeutic strategy for reducing plasma TG and VLDL in dyslipidemic individuals, and treatment can concurrently raise HDL-C levels with no adverse effects on LDL-C.

Example 10

ISIS 304801 Phase I Clinical Trial

In a double-blind, single and multiple ascending-dose (SAD and MAD) Phase 1 study, healthy subjects, aged 18 to 55 years, were randomly assigned in a 3:1 ratio to receive ISIS 304801 or placebo (normal saline).

SAD subjects were administered a single subcutaneous (SC) injection of 50, 100, 200, or 400 mg (n=4/cohort) at the Study Center. The subjects returned to the Study Center for an outpatient visit on Days 4 and 8 (±24 hour window) for blood sampling and for clinical evaluation. The subjects were followed until Day 15 when they were evaluated by a telephone interview.

MAD subjects were administered multiple SC injections at 50, 100, 200, and 400 mg at the Study Center. The subjects received a loading regimen of 3 doses the first week (Days 1, 3 and 5) followed by once weekly dosing for 3 weeks (Days 8, 15 and 22). The subjects were followed for 8 weeks after their last dose of study drug. The subjects returned to the Study Center for an outpatient visit on Days 29, 36 and 50 (±24 hour window) for safety and clinical laboratory evaluations and for blood sampling for PK analysis. The subjects were followed until Day 78 (±7 day window) when they were evaluated by a telephone interview.

The MAD subjects stayed at the Study Center from days −1 to 6 and days 22 to 23, where they were provided the diet shown in Table 33. The subjects fasted for at least 12 hours before blood samples were taken for evaluation at Days 5, 8, 15, 22, 23, 29, 36, 43 and 50 (±24 hour window).

TABLE 33

Study Center Patient Diet

| Study Day | Serving Portion | Food Description |
|---|---|---|
| Day −1 [Admit] | 525 ml. | Thai noodles with Beef & mixed vegetable, broccoli, bean sprout, green & red peppers |
|  | 375 ml. | Fresh fruit salad |
|  | 300 ml. | Orange juice |
|  | 1 | Horse shoe cake |
|  | 250 ml. | 2% Milk |
| Day 1 | 1 | Butter croissant |
|  | 2 | Eggs, Scrambled |
|  | 250 ml. | Sliced peaches with syrup |
|  | 300 ml. | Orange juice |
|  | 75 g. | Grilled Chicken Breast [Sandwich] on Kaiser bun |
|  | 1.5 cup | Cream of Mushroom Soup |
|  | 1-pkg. | Crackers |
|  | Small | Salad |
|  | On side | Condiments |
|  | 355 ml. | Ginger Ale |
|  | 75 g. | Roast Beef |
|  | 250 ml. | Mashed Potatoes |
|  | 375 ml. | Mixed Vegetables |
|  | On side | Gravy |
|  | On side | Garlic bread |
|  | 300 ml. | Apple juice |
|  | 1 | Carrot muffin |
|  | 250 ml. | 2% Milk |
| Day 2 | 3 | Pancakes |
|  | On side | Syrup |
|  | 1 | Banana |
|  | 300 ml. | Orange juice |
|  | 9" | Mesquite Chicken, Chicken, bacon, cheddar, tomato, red onion, & lettuce on whole wheat bread |
|  | On side | Ranch dressing |
|  | Cup | Broccoli & cheese soup |
|  | 1-pkg. | Crackers |
|  | 355 ml. | Ginger ale |

TABLE 33-continued

Study Center Patient Diet

| Study Day | Serving Portion | Food Description |
|---|---|---|
| | 375 g. | Beef Stir-fry & mixed vegetables, broccoli, carrots, celery, & onions |
| | 150 g. | Steamed rice |
| | 1-pkg. | Raisin |
| | 300 ml. | Apple juice |
| | 250 ml. | Fresh fruit salad |
| | 300 ml. | Cranberry juice |
| Day 3 | Med. | Cheese & vegetable omelet on whole wheat bagel toasted |
| | 300 ml. | Grape juice |
| | 9" | Black Angus Steak, mozzarella, cheddar, sauteed onion & mushrooms on Cheese bread |
| | On side | Honey Bourbon Mustard, Zesty Grille Sauce |
| | Cup | Chicken noodle soup |
| | 1-pkg. | Crackers |
| | 355 ml. | Ginger ale |
| | 400 g. | BBQ Chicken Breast, Vegetables, cooked mixed, cauliflower, carrots, red & green peppers, green beans |
| | 1.5 cups | Flavored rice |
| | 1-pkg. | Grapes |
| | 300 ml. | Apple juice |
| | 1 | Raisin Oatmeal cookie |
| | 250 ml. | 2% milk |
| Day 4 | 1 | Cheese Croissant |
| | 250 ml. | Sliced Peaches in syrup |
| | 300 ml. | Orange juice |
| | 2 | Flatbread Sammie, with Chicken, bacon, cheddar, tomato & romaine lettuce |
| | On side | Buttermilk ranch dressing |
| | Cup | Broccoli & Cheese soup |
| | 1-pkg. | Crackers |
| | 355 ml. | Ginger ale |
| | 425 g. | Beef Stew, tender Beef cubes, with carrots, onions, & potatoes |
| | 325 g. | Thai salad, with romaine lettuce, pasta, & dressings |
| | 1 | Italian bread |
| | 250 ml. | Sliced Pears in syrup |
| | 300 ml. | Apple juice |
| | 1 | Blueberry muffin |
| | 250 ml. | 2% Milk |
| Day 5 | 375 ml. | Corn Flakes |
| | Med. | Banana |
| | 250 ml. | 2% Milk |
| | 300 ml. | Apple juice |
| | 6 pcs. | Chicken wings |
| | 250 ml. | Fried rice |
| | 250 ml. | Mixed cooked veggies, green beans, carrots, & red peppers with sundried tomato sauce |
| | 355 ml. | 7-up |
| | 6" Pizza | Pepperoni lovers Pizza a double helping of deli style pepperoni & 100% Pizza Mozzarella |
| | Small | Salad |
| | 355 ml. | Ginger Ale |
| | 1 | Almond Croissant |
| | 250 ml. | 2% Milk |
| Day 6 [Discharge] | 45 g. | Bagel with Cream Cheese |
| | 300 ml. | Orange juice |
| Day 22 | 450 g. | Breakfast Omelets Spinach & Feta cheese |
| | 2 slices | Brown toast |
| | 300 ml. | Orange juice |
| | 9" | Zesty Grille Steak Prime Rib Steak, mozzarella, cheddar, mushroom, sauteed onion, on Cheese bread |
| | On side | Honey Bourbon Mustard, Zesty Grille Sauce |
| | Cup | Broccoli & Cheese soup |
| | 1-pkg. | Crackers |
| | 355 ml. | Ginger Ale |
| | 400 g. | Herb Grilled Chicken Breast with Vegetables |
| | 1.5 cups | Flavored rice |
| | Small | Fresh fruit salad |
| | 300 ml. | Apple juice |
| | 1 | Raisin Oatmeal cookie |
| | 250 ml. | 2% Milk |
| Day 23 [Discharge] | 45 g. | Butter croissant |
| | 300 ml. | Orange juice |

Results

Overall, ISIS 304801 demonstrated a good safety profile and was well tolerated in all subjects with no clinically meaningful elevations of transaminase enzymes and no significant adverse events.

The baseline characteristics of MAD cohorts are shown in Table 34. MAD subjects showed dose-dependent sustained reductions in total apoC-III and TG levels expressed as a percentage change from baseline in Tables 35-36.

TABLE 34

Baseline Characteristics of MAD Cohorts

|  | Placebo (n = 4) | 50 mg (n = 3) | 100 mg (n = 3) | 200 mg (n = 3) | 400 mg (n = 3) |
| --- | --- | --- | --- | --- | --- |
| Gender (M:F) | 3:1 | 3:0 | 3:0 | 3:0 | 3:0 |
| Age (yrs) | 43.0 | 40.0 | 40.0 | 43.0 | 40.0 |
| BMI (kg/m2) | 27.7 | 24.0 | 27.3 | 28.0 | 27.5 |
| Lipids & Lipoproteins, mg/dL | | | | | |
| Apo CIII | 6.3 | 10.4 | 9.5 | 11.6 | 8.7 |
| Triglycerides | 97 | 124 | 94 | 195 | 89 |
| Total Cholesterol | 195 | 157 | 196 | 185 | 181 |
| HDL-C | 45 | 42 | 46 | 43 | 62 |
| Non-HDL-C | 136 | 118 | 150 | 149 | 126 |
| LDL-C | 112 | 93 | 131 | 95 | 102 |

Per-protocol population. Values presented are the median.

TABLE 35

Dose-Dependent Prolonged Reduction in Serum ApoCIII:
Median % change in ApoCIII from Baseline

| Study Day | Placebo | 50 mg | 100 mg | 200 mg | 400 mg |
| --- | --- | --- | --- | --- | --- |
| Day 5 | 38.6 | 33.4 | −4.5 | −10.8 | −42.6 |
| Day 8 | 31.9 | 17.8 | −5.2 | −36.0 | −78.6 |
| Day 15 | 0.0 | −22.1 | −24.0 | −54.1 | −79.8 |
| Day 22 | 11.7 | −20.9 | −21.0 | −61.7 | −86.4 |
| Day 23 | 15.8 | −15.6 | −11.9 | −58.7 | −79.0 |
| Day 29 | −11.0 | −19.7 | −17.3 | −70.5 | −77.5 |
| Day 36 | 1.9 | −26.6 | −32.1 | −57.3 | −69.5 |
| Day 50 | 16.4 | 21.9 | −3.9 | −63.0 | −78.6 |

TABLE 36

Dose-Dependent Reductions in Triglycerides:
Median % Change in Triglycerides from Baseline

| Study Day | Placebo | 50 mg | 100 mg | 200 mg | 400 mg |
| --- | --- | --- | --- | --- | --- |
| Day 5 | 78.5 | 50.0 | 15.9 | −15.6 | −7.7 |
| Day 8 | 34.9 | 17.7 | −24.5 | −31.8 | −38.5 |
| Day 15 | 21.2 | −27.4 | −12.8 | −50.8 | −46.2 |
| Day 22 | 12.2 | −18.3 | −9.8 | −25.1 | −53.8 |
| Day 23 | 51.8 | −4.0 | 1.1 | −41.0 | −44.2 |
| Day 29 | 28.5 | −19.5 | −25.0 | −43.1 | −43.8 |
| Day 36 | 15.4 | −33.1 | −34.8 | −17.9 | −36.5 |
| Day 50 | 33.1 | 48.8 | −23.9 | −48.2 | −48.1 |

Median percent change from baseline values in the 50, 100, 200 and 400 mg multiple-dose groups showed reductions of total apoC-III of 20, 17, 71, and 78% and of TG of 20, 25, 43, and 44%, respectively, one week (Day 29) after the last dose. Reductions were sustained for at least four weeks after the last dose in the higher dose groups.

TG levels spiked at Day 5 and 23 for the placebo group, coinciding with the subjects' overnight stays at the Study Center. It is thought that the diet provided by the Study Center led to the surge in TG levels in the subjects staying overnight at the Study Center. ISIS 304801 decreased the TG spike in a dose-dependent manner. In a manner, the results shown herein, indicate a postprandial effect on TG (although TG levels were assessed after a 12 hour fast) by ISIS 304801 as a diet induced surge in TG was decreased in a dose-dependent manner by ISIS 304801.

LDL-C values did not change (data not shown) while HDL-C values tended to increase in a treatment-dependent manner as shown in Table 37.

TABLE 37

No Deleterious Effects on HDL-C

| Study Day | Placebo | 50 mg | 100 mg | 200 mg | 400 mg |
| --- | --- | --- | --- | --- | --- |
| Day 5 | −5.9 | 7.7 | −3.1 | −3.2 | −16.1 |
| Day 8 | 2.1 | 2.4 | 0.0 | −11.1 | −2.9 |
| Day 15 | −2.8 | 4.8 | 10.9 | 4.7 | −9.7 |
| Day 22 | −0.6 | 4.8 | 8.7 | 11.6 | −2.0 |
| Day 23 | 0.7 | 7.1 | 12.5 | 19.4 | −1.6 |
| Day 29 | 2.1 | 19.0 | 0.0 | 13.9 | 8.0 |
| Day 36 | 0.0 | 23.8 | 8.8 | 13.9 | 1.6 |
| Day 50 | −4.8 | 16.7 | 5.9 | 25.0 | 14.5 |

Example 11

ISIS 304801 Phase II Clinical Trial

A randomized, double-blind, placebo-controlled, dose response study is planned to evaluate the dose/response pharmacodynamic effects of ISIS 304801 vs. placebo on fasting apoC-III associated with VLDL levels. Additional endpoints to evaluate include: the pharmacodynamic effects of ISIS 304801 vs. placebo on fasting total apoC-III, TG, apoC-II (total and associated with VLDL), apolipoprotein B-100 (apoB-100), apolipoprotein A-1 (apoA-1), apolipoprotein A-2 (apoA-2), apolipoprotein E (apoE), total cholesterol (TC), low-density lipoprotein-cholesterol (LDL-C), LDL-TG, VLDL-C, VLDL-TG, non-high-density lipoprotein-cholesterol (non-HDL-C), non-HDL-TG, HDL-C, HDL-TG, chylomicron-C (CM-C), CM-TG, free fatty acids (FFA), and glycerol levels; the post-prandial lipid, apolipoprotein and lipoprotein characteristics and kinetics, and glucose levels in a subset of the patients in the study and assess more extensive PK in another subset of the patients (will not be the same patients as those undergoing the post-prandial assessment); and, the safety, tolerability and PK of ISIS 304801.

For each patient, the participation period consists of a ≤5-week screening period, (which includes a 4-week tight diet control run-in qualification period), a 1-week study qualification/baseline assessment period, a 13-week treatment period, and a post-treatment evaluation period of 13 weeks, for a total of 32 weeks of study participation. Concomitant medications and adverse events (AEs) will be recorded throughout all periods of the study.

Patients will be at least 18 years of age and have fasting TG ≥500 mg/dL at screening and fasting TG ≥300 mg/dL and ≤2000 mg/dL after 4-weeks of tight diet control run-in.

Seventy two (72) patients are planned for this study. There will be 24 patients planned per dose cohort (100, 200, 300 mg) with 18 ISIS 304801 (active) and 6 placebo patients per cohort. Eligible patients will be enrolled equally (1:1) into a non-extensive PK/post-prandial group (Group 1) or an extensive PK/post-prandial group (Group 2). Patients in Group 2 will be randomized equally (1:1) to an extensive PK group (Group 2a) or a post-prandial assessment group (Group 2b). Group 2a patients will be randomized equally (1:1:1) to 1 of the 3 dose cohorts (100, 200, 300 mg) and, within each dose cohort, 5:1 to receive active or placebo. Group 2b patients will be randomized equally (1:1) to 1 of 2 dose cohorts (200, 300 mg) and, within each dose cohort, 2:1 to receive active or placebo. Group 1 patients will be randomized to dose cohort and treatment in a manner that achieves an overall study randomization of 1:1:1 to dose cohort (100, 200, 300 mg) and 3:1 to treatment (active, placebo).

Patients will be placed on a tightly controlled diet (after screening procedures are performed) for the duration of study participation. After 28 days on the controlled diet, patients will have baseline measurements and be assessed for qualification of enrollment into the treatment phase of the study. Patients who meet the enrollment criteria following diet run-in will be enrolled equally (1:1) into a non-extensive PK/post-prandial group (Group 1) or into an extensive PK/post-prandial group (Group 2) and randomized within their Group assignment.

Study Drug and Treatment

A solution of ISIS 304801 (200 mg/mL, 1.0 mL) contained in 2-mL stoppered glass vials will be provided.

The placebo for this study will be 0.9% sterile saline. ISIS 304801 solution and placebo will be prepared by an unblinded pharmacist (or qualified delegate). Vials are for single-use only. A trained professional, blinded to the identity of the drug, will administer the Study Drug. The Study Drug will be administered as a SC injection in the abdomen, thigh, or outer area of the upper arm on each dosing day. Doses of 100 and 200 mg will be administered as a single SC injection. Doses of 300 mg will be administered as two equal volume noncontiguous SC injections.

Patients will receive 13 doses of Study Drug administered by SC injection once a week for 13 weeks (Days 1, 8, 15, 22, 29, 36, 43, 50, 57, 64, 71, 78, and 85).

Patients will complete the treatment visits on Day 1±0 days and on Day 8, 15, 22, 29, 36, 43, 50, 57, 64, 71, 78, and 85 within ±1 day. Patients in the extensive PK group will also visit the clinic on Day 2 and 86±0 days relative to Day 1 and 85, respectively, for the 24 hour blood draw. Patients will complete the follow-up visits on Day 92 and 99 within ±1 day, Day 127 within ±3 days, and Day 176 within ±5 days of the scheduled visit date. Patients in the post-prandial assessment group will also visit the clinic on Day 103 within ±2 days and on the day following the Day 103 visit for the 24 hour blood draw.

Preceding each visit that includes a blood draw for pharmacodynamic measurements (Days 8, 15, 29, 43, 57, 71, and 85), patients will be provided a standardized pre-cooked meal for the dinner on the evening prior to their visit (to ensure equal moderation of fat intake, per patient and per time point) after which they will remain fasted. Alcohol consumption will not be allowed for 48 hrs preceding these clinic visits.

Blood will be collected for measurement of VLDL apoC-III and other pharmacodynamic markers on Days 8, 15, 29, 43, 57, 71, and 85 (prior to Study Drug administration).

Patients in the post-prandial assessment group will consume standardized pre cooked meals (lunches and dinners (provided) and instructions for breakfasts and snacks) for the 2 days prior to the post-prandial evaluations. On each of the post-prandial evaluation days, following the blood draws, patients will consume a standardized liquid meal, which represents about a third of the daily caloric requirements, with a stable radioisotope tracer, followed by serial blood sampling. Patients will receive a standardized pre-cooked meal 9 hrs after consuming the liquid meal, after which they will fast until the 24 hour blood draw the following day.

In addition to trough sample collection, patients in the extensive PK assessment group will undergo serial blood sampling for 24 hrs after their first (Day 1-2) and last (Day 85-86) dose of Study Drug.

Post-treatment Evaluation Period

Patients will be followed until Study Day 176. During this time, patients will return to the study center for outpatient clinic visits on Study Days 92, 99, 127, and 176 (and Day 103 for patients in the post-prandial assessment group) for safety and clinical laboratory evaluations (blood draws), diet counseling and monitoring, concomitant medication usage recording, and AE event collection.

Blood samples for PK and PD analysis will be collected periodically throughout the post-treatment evaluation period. Laboratory measurements of serum chemistry, urinalysis, coagulation, complement, hematology, immune function, thyroid function, and full lipid panel will be performed at the various times throughout the study.

Post-prandial assessments will be done in a subset of patients as described below.

Post-prandial Meal, Sampling Schedule, and Assessment

Post-prandial assessment for lipoproteins metabolism will be performed using a radiolabelled meal supplemented with a labeled tracer, 3H-palmitate (300 µCi, Perkin Elmer Inc., Woodbridge, ON, Canada), sonicated into the liquid meal. Palmitate is a fatty acid that is a common constituent of any diet. The 3H-palmitate tracer emits weak radioactivity, equivalent to an X-ray. Since dietary palmitate is incorporated into chylomicrons as they are formed in the enterocytes of the gut, this enables monitoring the appearance and clearance of newly-formed chylomicrons from circulation. The methodology to be applied for studying post-prandial kinetics of chylomicrons appearance and clearance is well-established (Mittendorfer et al. 2003, Diabetes, 52: 1641-1648; Bickerton et al. 2007; Normand-Lauziere et al. 2010, PLoS. One, 5: e10956).

A liquid meal (similar to a milkshake) containing a small amount (300 µCi) of radiolabelled fatty acids (3H-palmitate) will be provided. The liquid meal will provide about a third of the daily caloric requirements. From 1 hr prior to 9 hrs after the ingestion of the meal, a constant infusion of [U-13C]-K palmitate (0.01 µmol/kg/min in 100 ml 25% human serum albumin; Cambridge Isotopes Laboratories Inc., Andover, Mass.) and a primed (1.6 µmol/kg) continuous (0.05 µmol/kg/min) infusion of [1,1,2,3,3-2H]-glycerol (Cambridge Isotopes Laboratories Inc.) will be administered as previously described (Normand-Lauziere et al. 2010, PLoS. One, 5: e10956). Plasma palmitate and glycerol appearance rates will be calculated using Steele's non-steady state equation assuming a volume of distribution of 90 ml/kg and 230 ml/kg, respectively (Gastaldelli et al. 1999, J Appl. Physiol, 87: 1813-1822).

Blood samples will be drawn at intervals before and after the ingestion of the radiolabelled meal on days prior to and after the Treatment phase as noted in the table below. A standardized meal will be given to the participants after the 9 hr blood draw. Blood will be collected in tubes containing Na2 EDTA and Orlistat (30 µg/ml, Roche, Mississauga, Canada) to prevent in vitro triacylglycerol lipolysis and separate samples will be collected in NaF tubes for plasma glucose determination.

The following will be measured at each time-point:
Plasma and CM fraction levels for 3H-tracer
Plasma [U-13C]-K palmitate and [1,1,2,3,3-2H]-glycerol appearance rates Plasma and CM fraction levels for TG, TC, and apoB
Plasma and VLDL fraction levels for apo CIII, apo CII, and apo E
Plasma levels for glucose Plasma samples may also be used for profiling of drug binding proteins, bioanalytical method validation purposes, stability and metabolite assessments, or to assess other actions of ISIS 304801 with plasma constituents.

What is claimed is:

1. A method of increasing high density lipoprotein (HDL) levels in a human, comprising administering to a human in need thereof an antisense compound, wherein the antisense compound is a single-stranded oligonucleotide 12 to 30 nucleobases in length targeted to human apolipoprotein C-III (ApoCIII), whereby HDL levels are increased by at least 20% in the human.

2. The method of claim 1, wherein the oligonucleotide targeting ApoCIII is a modified single-stranded oligonucleotide.

3. The method of claim 2, wherein the modified oligonucleotide has a nucleobase sequence at least 90% or 100% complementary to a nucleobase sequence of SEQ ID NO: 1.

4. The method of claim 2, wherein the modified oligonucleotide consists of 20 linked nucleosides.

5. The method of claim 2, wherein at least one internucleoside linkage of the modified oligonucleotide is a modified internucleoside linkage, at least one nucleoside of the modified oligonucleotide comprises a modified sugar and/or at least one nucleoside of the modified oligonucleotide comprises a modified nucleobase.

6. The method of claim 5, wherein each modified internucleoside linkage of the modified oligonucleotide is a phosphorothioate internucleoside linkage.

7. The method of claim 5, wherein at least one modified sugar is a bicyclic sugar.

8. The method of claim 5, wherein at least one modified sugar comprises a 2'-O-methyoxyethyl.

9. The method of claim 5, wherein the modified nucleobase is a 5-methylcytosine.

10. The method of claim 2, wherein the modified oligonucleotide comprises:
(a) a gap segment consisting of linked deoxynucleosides;
(b) a 5' wing segment consisting of linked nucleosides;
(c) a 3' wing segment consisting linked nucleosides;
wherein the gap segment is positioned immediately adjacent to and between the 5' wing segment and the 3' wing segment and wherein each nucleoside of each wing segment comprises a modified sugar.

11. The method of claim 2, wherein the modified oligonucleotide comprises:
(a) a gap segment consisting of 10 linked deoxynucleosides;
(b) a 5' wing segment consisting of 5 linked nucleosides;
(c) a 3' wing segment consisting 5 linked nucleosides;
wherein the gap segment is positioned immediately adjacent to and between the 5' wing segment and the 3' wing segment and wherein each nucleoside of each wing segment comprises a 2'-O-methyoxyethyl sugar, wherein each cytosine is a 5'-methylcytosine, and wherein each internucleoside linkage is a phosphorothioate linkage.

12. The method of claim 1, wherein the compound is parenterally administered.

13. The method of claim 12, wherein the parenteral administration is subcutaneous administration.

14. The method of claim 1, further comprising administering a second agent.

15. The method of claim 14, wherein the second agent is selected from among siRNA targeting ApoCIII, an anti-ApoCIII antibody, an ApoCIII peptide inhibitor, an ApoCIII lowering agent, a cholesterol lowering agent, a non-HDL lipid lowering agent, a LDL lowering agent, a HDL raising agent, fish oil, a statin, niacin, a fibrate, DCCR (salt of diazoxide), an anti-diabetic agent, a glucose lowering agent and an anti-inflammatory agent.

16. A method of reducing chylomicronemia in a human, comprising administering to a human in need thereof an antisense compound, wherein the antisense compound is a single-stranded oligonucleotide 12 to 30 nucleobases in length targeted to human apolipoprotein C-III (ApoCIII), whereby chylomicronemia is reduced in the human.

17. The method of claim 16, wherein the antisense compound targeting ApoCIII is a modified single-stranded oligonucleotide.

18. The method of claim 17, wherein the modified oligonucleotide has a nucleobase sequence at least 90% or 100% complementary to a nucleobase sequence of SEQ ID NO: 1.

19. The method of claim 17, wherein the modified oligonucleotide consists of 20 linked nucleosides.

20. The method of claim 17, wherein at least one internucleoside linkage of the modified oligonucleotide is a modified internucleoside linkage, at least one nucleoside of the modified oligonucleotide comprises a modified sugar and/or at least one nucleoside of the modified oligonucleotide comprises a modified nucleobase.

21. The method of claim 20, wherein each modified internucleoside linkage of the modified oligonucleotide is a phosphorothioate internucleoside linkage.

22. The method of claim 20, wherein at least one modified sugar is a bicyclic sugar.

23. The method of claim 20, wherein at least one modified sugar comprises a 2'-O-methyoxyethyl.

24. The method of claim 20, wherein the modified nucleobase is a 5-methylcytosine.

25. The method of claim 17, wherein the modified oligonucleotide comprises:
(g) a gap segment consisting of linked deoxynucleosides;
(h) a 5' wing segment consisting of linked nucleosides;
(i) a 3' wing segment consisting linked nucleosides;
wherein the gap segment is positioned immediately adjacent to and between the 5' wing segment and the 3' wing segment and wherein each nucleoside of each wing segment comprises a modified sugar.

26. The method of claim 17, wherein the modified oligonucleotide comprises:
(g) a gap segment consisting of 10 linked deoxynucleosides;
(h) a 5' wing segment consisting of 5 linked nucleosides;
(i) a 3' wing segment consisting 5 linked nucleosides;
wherein the gap segment is positioned immediately adjacent to and between the 5' wing segment and the 3' wing segment and wherein each nucleoside of each wing segment comprises a 2'-O-methyoxyethyl sugar, wherein each cytosine is a 5'-methylcytosine, and wherein each internucleoside linkage is a phosphorothioate linkage.

27. The method of claim 16, wherein the compound is parenterally administered.

28. The method of claim 27, wherein the parenteral administration is subcutaneous administration.

29. The method of claim 16, further comprising administering a second agent.

30. The method of claim 29, wherein the second agent is selected from among siRNA targeting ApoCIII, an anti-ApoCIII antibody, an ApoCIII peptide inhibitor, an ApoCIII lowering agent, a cholesterol lowering agent, a non-HDL lipid lowering agent, a LDL lowering agent, a HDL raising agent, fish oil, a statin, niacin, a fibrate, DCCR (salt of diazoxide), an anti-diabetic agent, a glucose lowering agent and an anti-inflammatory agent.

31. A method of reducing pancreatitis in a human, comprising administering to a human in need thereof an antisense compound, wherein the antisense compound is a single-stranded oligonucleotide 12 to 30 nucleobases in length targeted to human apolipoprotein C-III (ApoCIII), whereby pancreatitis is reduced in the human.

32. The method of claim 31, wherein the antisense compound targeting ApoCIII is a modified single-stranded oligonucleotide.

33. The method of claim 32, wherein the modified oligonucleotide has a nucleobase sequence at least 90% or 100% complementary to a nucleobase sequence of SEQ ID NO: 1.

34. The method of claim 32, wherein the modified oligonucleotide consists of 20 linked nucleosides.

35. The method of claim 32, wherein at least one internucleoside linkage of the modified oligonucleotide is a modified internucleoside linkage, at least one nucleoside of the modified oligonucleotide comprises a modified sugar and/or at least one nucleoside of the modified oligonucleotide comprises a modified nucleobase.

36. The method of claim 35, wherein each modified internucleoside linkage of the modified oligonucleotide is a phosphorothioate internucleoside linkage.

37. The method of claim 35, wherein at least one modified sugar is a bicyclic sugar.

38. The method of claim 35, wherein at least one modified sugar comprises a 2'-O-methoxyethyl.

39. The method of claim 35, wherein the modified nucleobase is a 5-methylcytosine.

40. The method of claim 32, wherein the modified oligonucleotide comprises:
   (j) a gap segment consisting of linked deoxynucleosides;
   (k) a 5' wing segment consisting of linked nucleosides;
   (l) a 3' wing segment consisting linked nucleosides;
wherein the gap segment is positioned immediately adjacent to and between the 5' wing segment and the 3' wing segment and wherein each nucleoside of each wing segment comprises a modified sugar.

41. The method of claim 32, wherein the modified oligonucleotide comprises:
   (j) a gap segment consisting of 10 linked deoxynucleosides;
   (k) a 5' wing segment consisting of 5 linked nucleosides;
   (l) a 3' wing segment consisting 5 linked nucleosides;
wherein the gap segment is positioned immediately adjacent to and between the 5' wing segment and the 3' wing segment and wherein each nucleoside of each wing segment comprises a 2'-O-methoxyethyl sugar, wherein each cytosine is a 5'-methylcytosine, and wherein each internucleoside linkage is a phosphorothioate linkage.

42. The method of claim 31, wherein the compound is parenterally administered.

43. The method of claim 42, wherein the parenteral administration is subcutaneous administration.

44. The method of claim 31, further comprising administering a second agent.

45. The method of claim 44, wherein the second agent is selected from among siRNA targeting ApoCIII, an anti-ApoCIII antibody, an ApoCIII peptide inhibitor, an ApoCIII lowering agent, a cholesterol lowering agent, a non-HDL lipid lowering agent, a LDL lowering agent, a HDL raising agent, fish oil, a statin, niacin, a fibrate, DCCR (salt of diazoxide), an anti-diabetic agent, a glucose lowering agent and an anti-inflammatory agent.

* * * * *

SEQUENCE LISTING

<160> NUMBER OF SEQ ID NOS: 5

<210> SEQ ID NO 1
<211> LENGTH: 533
<212> TYPE: DNA
<213> ORGANISM: Homo sapiens

<400> SEQUENCE: 1

```
tgctcagttc atccctagag gcagctgctc caggaacaga ggtgccatgc agccccgggt    60
actccttgtt gttgccctcc tggcgctcct ggcctctgcc cgagcttcag aggccgagga   120
tgcctccctt ctcagcttca tgcagggtta catgaagcac gccaccaaga ccgccaagga   180
tgcactgagc agcgtgcagg agtcccaggt ggcccagcag gccaggggct gggtgaccga   240
tggcttcagt tccctgaaag actactggag caccgttaag gacaagttct ctgagttctg   300
ggatttggac cctgaggtca gaccaacttc agccgtggct gcctgagacc tcaataccc    360 aagtccacct gcctatccat cctgcgagct ccttgggtcc tgcaatctcc agggctgccc   420
ctgtaggttg cttaaaaggg acagtattct cagtgctctc ctaccccacc tcatgcctgg   480 ccccctcca ggcatgctgg cctcccaata aagctggaca agaagctgct atg           533
```

<210> SEQ ID NO 2
<211> LENGTH: 3964
<212> TYPE: DNA
<213> ORGANISM: Homo sapiens

<400> SEQUENCE: 2

```
ctactccagg ctgtgttcag ggcttggggc tggtggaggg aggggcctga aattccagtg    60
tgaaaggctg agatgggccc gaggcccctg gcctatgtcc aagccatttc ccctctcacc   120
agcctctccc tggggagcca gtcagctagg aaggaatgag ggctccccag gcccacccc    180 agttcctgag ctcatctggg ctgcagggct ggcgggacag cagcgtggac tcagtctcct   240
agggatttcc caactctccc gcccgcttgc tgcatctgga caccctgcct caggccctca   300
tctccactgg tcagcaggtg acctttgccc agcgccctgg gtcctcagtg cctgctgccc   360
tggagatgat ataaaacagg tcagaaccct cctgcctgtc tgctcagttc atccctagag   420
gcagctgctc caggtaatgc cctctgggga ggggaaagag gaggggagga ggatgaagag   480
gggcaagagg agctccctgc ccagcccagc cagcaagcct ggagaagcac ttgctagagc   540
taaggaagcc tcggagctgg acgggtgccc cccaccctc atcataacct gaagaacatg    600
gaggcccggg aggggtgtca cttgcccaaa gctacacagg gggtggggct ggaagtggct   660
ccaagtgcag gttccccct cattcttcag gcttagggct ggaggaagcc ttagacagcc     720
cagtcctacc ccagacaggg aaactgaggc ctggagaggg ccagaaatca cccaaagaca   780
cacagcatgt tggctggact ggacggagat cagtccagac cgcaggtgcc ttgatgttca   840
gtctggtggg ttttctgctc catcccaccc acctcccttt gggcctcgat ccctcgcccc   900
tcaccagtcc cccttctgag agcccgtatt agcagggagc cggccctac tccttctggc    960 agacccagct aaggttctac cttaggggcc acgccacctc cccagggagg ggtccagagg  1020 catgggacc tggggtgccc ctcacaggac acttccttgc aggaacagag gtgccatgca   1080
gccccgggta ctccttgttg ttgccctcct ggcgctcctg gcctctgccc gtaagcactt   1140
```

```
ggtgggactg ggctgggggc agggtggagg caacttgggg atcccagtcc caatgggtgg    1200
tcaagcagga gcccagggct cgtccagagg ccgatccacc ccactcagcc ctgctctttc    1260
ctcaggagct tcagaggccg aggatgcctc ccttctcagc ttcatgcagg gttacatgaa    1320
gcacgccacc aagaccgcca aggatgcact gagcagcgtg caggagtccc aggtggccca    1380
gcaggccagg tacacccgct ggcctccctc cccatccccc ctgccagctg cctccattcc    1440
cacccgcccc tgccctggtg agatcccaac aatggaatgg aggtgctcca gcctcccctg    1500
ggcctgtgcc tcttcagcct cctctttcct cacagggcct tgtcaggct gctgcgggag     1560 agatgacaga gttgagactg cattcctccc aggtccctcc tttctcccg gagcagtcct     1620 agggcgtgcc gttttagccc tcatttccat tttcctttcc tttcccttc tttctctttc     1680 tatttctttc tttctttctt tctttctttc tttctttctt tctttcttt tttctttctt     1740 tctttctttc ctttctttct ttcctttctt tctttccttt ctttctttct ttcctttctt    1800
tctctttctt tctttctttc cttttcttt ctttccctct cttcctttct ctctttcttt     1860
cttcttcttt ttttttaat ggagtctccc tctgtcacct aggctggagt gcagtggtgc     1920
catctcggct cactgcaacc tccgtctccc gggttcaacc cattctcctg cctcagcctc    1980
ccaagtagct gggattacag gcacgcgcca ccacacccag ctaattttg tatttttagc     2040 agagatgggg tttcaccatg ttggccaggt tggtcttgaa ttcctgacct caggggatcc    2100
tcctgcctcg gcctcccaaa gtgctgggat tacaggcatg agccactgcg cctggcccca    2160
ttttcctttt ctgaaggtct ggctagagca gtggtcctca gccttttgg caccagggac     2220 cagttttgtg gtggacaatt tttccatggg ccagcgggga tggttttggg atgaagctgt    2280
tccacctcag atcatcaggc attagattct cataaggagc cctccaccta gatccctggc    2340
atgtgcagtt cacaataggg ttcacactcc tatgagaatg taaggccact tgatctgaca    2400
ggaggcggag ctcaggcggt attgctcact cacccaccac tcacttcgtg ctgtgcagcc    2460
cggctcctaa cagtccatgg accagtacct atctatgact tgggggttgg ggaccctgg     2520 gctaggggtt tgccttggga ggccccacct gacccaattc aagcccgtga gtgcttctgc    2580
tttgttctaa gacctgggc cagtgtgagc agaagtgtgt ccttcctctc ccatcctgcc     2640
cctgcccatc agtactctcc tctccctac tcccttctcc acctcaccct gactggcatt     2700
agctggcata gcagaggtgt tcataaacat tcttagtccc cagaaccggc tttggggtag    2760
gtgttatttt ctcactttgc agatgagaaa attgaggctc agagcgatta ggtgacctgc    2820
cccagatcac acaactaatc aatcctccaa tgactttcca aatgagaggc tgcctccctc    2880
tgtcctaccc tgctcagagc caccaggttg tgcaactcca ggcggtgctg tttgcacaga    2940
aaacaatgac agccttgacc tttcacatct ccccaccctg tcactttgtg cctcaggccc    3000
aggggcataa acatctgagg tgacctggag atggcagggt ttgacttgtg ctggggttcc    3060
tgcaaggata tctcttctcc cagggtggca gctgtggggg attcctgcct gaggtctcag    3120
ggctgtcgtc cagtgaagtt gagagggtgg tgtggtcctg actggtgtcg tccagtgggg    3180
acatgggtgt gggtcccatg gttgcctaca gaggagttct catgccctgc tctgttgctt    3240
cccctgactg atttagggge tgggtgaccg atggcttcag ttccctgaaa gactactgga    3300
gcaccgttaa ggacaagttc tctgagttct gggatttgga ccctgaggtc agaccaactt    3360
cagccgtggt tgcctgagac ctcaatacce caagtccacc tgcctatcca tcctgcgagc    3420
tccttgggtc ctgcaatctc cagggctgcc cctgtaggtt gcttaaaagg gacagtattc    3480
```

```
tcagtgctct cctaccccac ctcatgcctg gcccccctcc aggcatgctg gcctcccaat    3540
aaagctggac aagaagctgc tatgagtggg ccgtcgcaag tgtgccatct gtgtctgggc    3600
atgggaaagg gccgaggctg ttctgtgggt gggcactgga cagactccag gtcaggcagg    3660
catggaggcc agcgctctat ccaccttctg gtagctgggc agtctctggg cctcagtttc    3720
ttcatctcta aggtaggaat caccctccgt accctgcctt ccttgacagc tttgtgcgga    3780
aggtcaaaca ggacaataag tttgctgata ctttgataaa ctgttaggtg ctgcacaaca    3840
tgacttgagt gtgtgcccca tgccagccac tatgcctggc acttaagttg tcatcagagt    3900
tgagactgtg tgtgtttact caaaactgtg gagctgacct ccctatcca ggcccctag     3960 ccct                                                                3964

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
agcttcttgt ccagctttat                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ccttccctga aggttcctcc                                                 20

<210> SEQ ID NO 5
<211> LENGTH: 524
<212> TYPE: DNA
<213> ORGANISM: Mus musculus

<400> SEQUENCE: 5
ctgctcagtt ttatccctag aagcagctag ctactccagg tacgtaggtg ccatgcagcc      60
ccggacgctc ctcactgtgg ccctcttggc tctcctggca tctgcccgag ctgaagaggt     120
agagggatcc ttgctgctgg gctctgtaca gggctacatg gaacaagcct ccaagacggt     180
ccaggatgcg ctaagtagcg tgcaggagtc cgatatagct gtggtggcca ggggctggat     240
ggacaatcac ttcagatccc tgaaaggcta ctggagcaag tttactgaca agttcaccgg     300
cttctgggat tctaaccctg aggaccaacc aactccagct attgagtcgt gagacttctg     360
tgttgcagat gtgcctgttc ctccatcctg ctgccccct ccaggcctgc caggtggccc     420
ctgaaggttg ctttaagggg aaagtatgtt ctcatgtctt caccctccc tagatctcac     480 ctaaacatgc tgtccctaat aaagctggat aagaagctgc tgtt                      524
```